(12) United States Patent
Mihashi et al.

(10) Patent No.: US 7,246,906 B2
(45) Date of Patent: Jul. 24, 2007

(54) CORRECTION-FACTOR DETERMINATION APPARATUS AND METHOD

(75) Inventors: Toshifumi Mihashi, Tokyo (JP); Yoko Hirohara, Tokyo (JP)

(73) Assignee: Kabushiki Kaisha Topcon, Tokyo (JP)

(*) Notice: Subject to any disclaimer, the term of this patent is extended or adjusted under 35 U.S.C. 154(b) by 284 days.

(21) Appl. No.: 10/527,447

(22) PCT Filed: Sep. 10, 2003

(86) PCT No.: PCT/JP03/11583

§ 371 (c)(1),
(2), (4) Date: Apr. 15, 2005

(87) PCT Pub. No.: WO2004/023990

PCT Pub. Date: Mar. 25, 2004

(65) Prior Publication Data

US 2005/0270490 A1 Dec. 8, 2005

(30) Foreign Application Priority Data

Sep. 13, 2002 (JP) ............................ 2002-268033

(51) Int. Cl.
*A61B 3/00* (2006.01)
(52) U.S. Cl. ...................................... 351/246
(58) Field of Classification Search ................ 359/246, 359/205, 206, 211, 212, 221, 237, 243
See application file for complete search history.

(56) References Cited

U.S. PATENT DOCUMENTS

| 4,385,813 A | 5/1983 | Klein et al. |
|---|---|---|
| 6,273,566 B1 | 8/2001 | Kobayashi et al. |
| 6,338,559 B1 | 1/2002 | Williams et al. |
| 6,460,997 B1 * | 10/2002 | Frey et al. ................. 351/211 |

| 2001/0056338 A1 | 12/2001 | Qi |

FOREIGN PATENT DOCUMENTS

| JP | 55-151937 A | 11/1980 |
|---|---|---|
| JP | 05-009092 B2 | 2/1993 |
| JP | 2001-095760 A | 4/2001 |
| JP | 2002-045336 A | 2/2002 |
| JP | 2002-204785 A | 7/2002 |
| JP | 2002-209854 A | 7/2002 |
| JP | 3347507 B2 | 9/2002 |
| JP | 2002-306416 A | 10/2002 |
| JP | 2002-306417 A | 10/2002 |

* cited by examiner

*Primary Examiner*—Ricky Mack
*Assistant Examiner*—Tuyen Tra
(74) *Attorney, Agent, or Firm*—Foley & Lardner LLP

(57) ABSTRACT

The low-order aberration leading to better visual acuity is calculated from the results of measurement of an eye characteristic by an eye characteristic measuring instrument that can measure up to the high-order aberration, and data on a correction factor is collected, thereby obtaining a result more approximate to the subjective value. According to at least measurement data representing the wave aberration of the eye being examined (S401, S403), an image data creating unit creates optotype retina image data by conducting simulation of the visual acuity of an optotype (S405), considering the correction factor for refraction correction. A correction factor setting unit sets a correction factor to be given to the image data creating unit (S417). A judging unit judges from the correction opotype retina image data corrected by the correction factor whether or not an adequate correction factor is set (S407 to S421). The correction factor setting unit sets a correction factor on the basis of the results of judgment by the judging unit, and changes the correction factor until the judging unit judge that the correction factor is adequate.

27 Claims, 21 Drawing Sheets

$$\begin{array}{ccl}
i & 2j-i & \\
0 & 0 & 1 \\
1 & -1 & r\sin(t) \\
1 & 1 & \cos(t)\,r \\
2 & -2 & r^2\sin(2t) \\
2 & 0 & 2r^2-1 \\
2 & 2 & r^2\cos(2t) \\
3 & -3 & r^3\sin(3t) \\
3 & -1 & (3r^3-2r)\sin(t) \\
3 & 1 & (3r^3-2r)\cos(t) \\
3 & 3 & r^3\cos(3t) \\
4 & -4 & r^4\sin(4t) \\
4 & -2 & (4r^4-3r^2)\sin(2t) \\
4 & 0 & 6r^4-6r^2+1 \\
4 & 2 & (4r^4-3r^2)\cos(2t) \\
4 & 4 & r^4\cos(4t) \\
5 & -5 & r^5\sin(5t) \\
5 & -3 & (5r^5-4r^3)\sin(3t) \\
5 & -1 & (10r^5-12r^3+3r)\sin(t) \\
5 & 1 & (10r^5-12r^3+3r)\cos(t) \\
5 & 3 & (5r^5-4r^3)\cos(3t) \\
5 & 5 & r^5\cos(5t) \\
6 & -6 & r^6\sin(6t) \\
6 & -4 & (6r^6-5r^4)\sin(4t) \\
6 & -2 & (15r^6-20r^4+6r^2)\sin(2t) \\
6 & 0 & 20r^6-30r^4+12r^2-1 \\
6 & 2 & (15r^6-20r^4+6r^2)\cos(2t) \\
6 & 4 & (6r^6-5r^4)\cos(4t) \\
6 & 6 & r^6\cos(6t)
\end{array}$$

FIG.3

| i | 2j−i | |
|---|------|---|
| 0 | 0 | $1$ |
| 1 | −1 | $y$ |
| 1 | 1 | $x$ |
| 2 | −2 | $2yx$ |
| 2 | 0 | $2x^2 + 2y^2 - 1$ |
| 2 | 2 | $x^2 - y^2$ |
| 3 | −3 | $3yx^2 - y^3$ |
| 3 | −1 | $3yx^2 + 3y^3 - 2y$ |
| 3 | 1 | $3x^3 + 3xy^2 - 2x$ |
| 3 | 3 | $x^3 - 3xy^2$ |
| 4 | −4 | $4yx^3 - 4y^3 x$ |
| 4 | −2 | $8yx^3 + 8y^3 x - 6yx$ |
| 4 | 0 | $6x^4 + 12x^2 y^2 + 6y^4 - 6x^2 - 6y^2 + 1$ |
| 4 | 2 | $4x^4 - 4y^4 - 3x^2 + 3y^2$ |
| 4 | 4 | $x^4 - 6x^2 y^2 + y^4$ |
| 5 | −5 | $5yx^4 - 10y^3 x^2 + y^5$ |
| 5 | −3 | $15yx^4 + 10y^3 x^2 - 5y^5 - 12yx^2 + 4y^3$ |
| 5 | −1 | $10yx^4 + 20y^3 x^2 + 10y^5 - 12yx^2 - 12y^3 + 3y$ |
| 5 | 1 | $10x^5 + 20x^3 y^2 + 10xy^4 - 12x^3 - 12xy^2 + 3x$ |
| 5 | 3 | $5x^5 - 10x^3 y^2 - 15xy^4 - 4x^3 + 12xy^2$ |
| 5 | 5 | $x^5 - 10x^3 y^2 + 5xy^4$ |
| 6 | −6 | $6yx^5 - 20y^3 x^3 + 6y^5 x$ |
| 6 | −4 | $24yx^5 - 24y^5 x - 20yx^3 + 20y^3 x$ |
| 6 | −2 | $30yx^5 + 60y^3 x^3 + 30y^5 x - 40yx^3 - 40y^3 x + 12yx$ |
| 6 | 0 | $20x^6 + 60x^4 y^2 + 60x^2 y^4 + 20y^6 - 30x^4 - 60x^2 y^2 - 30y^4 + 12x^2 + 12y^2 - 1$ |
| 6 | 2 | $15x^6 + 15x^4 y^2 - 15x^2 y^4 - 15y^6 - 20x^4 + 20y^4 + 6x^2 - 6y^2$ |
| 6 | 4 | $6x^6 - 30x^4 y^2 - 30x^2 y^4 + 6y^6 - 5x^4 + 30x^2 y^2 - 5y^4$ |
| 6 | 6 | $x^6 - 15x^4 y^2 + 15x^2 y^4 - y^6$ |

FIG.4

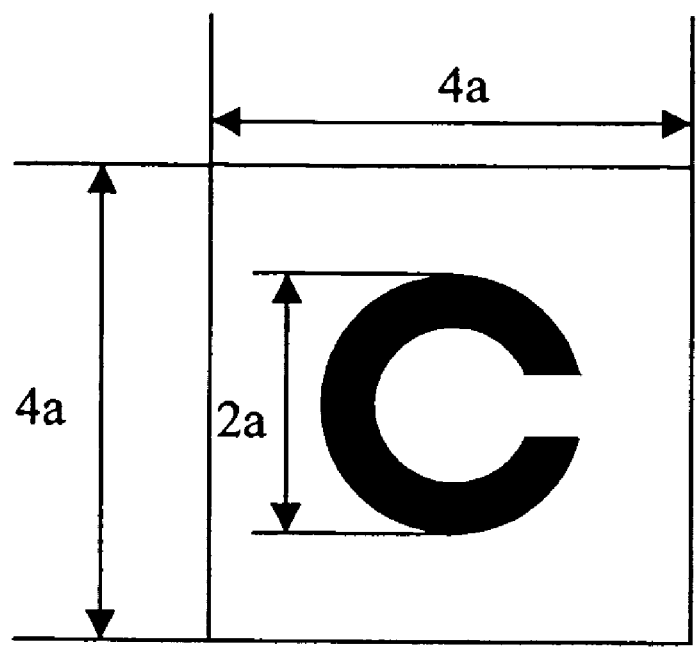
ORIGINAL LANDOLT'S
RING IMAGE
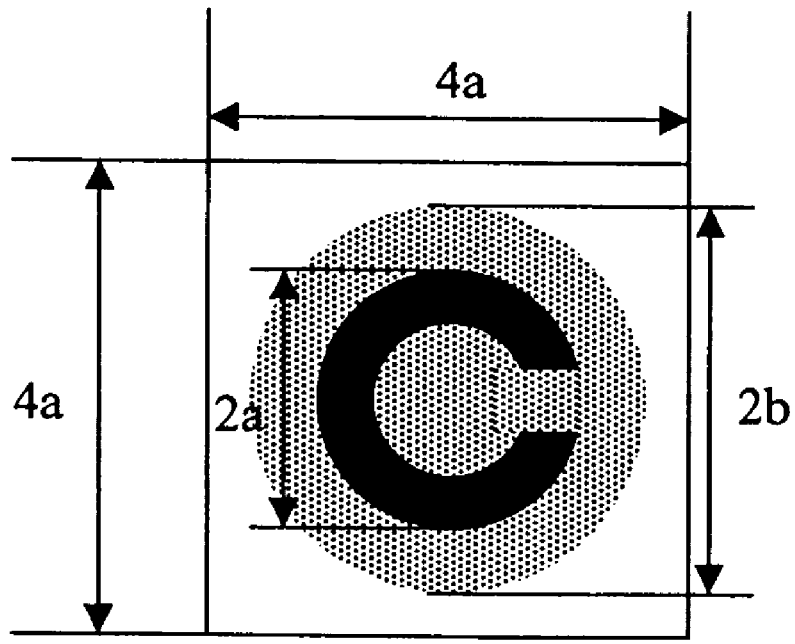
TEMPLATE IMAGE
Fig.9

CORRECTION-FACTOR DETERMINATION APPARATUS AND METHOD

TECHNICAL FIELD

The present invention relates to correction-factor determination apparatuses and methods, and more particularly, to a correction-factor determination apparatus and method for objectively performing measurement close to a subjective value, according to wavefront aberrations

BACKGROUND ART

Conventionally, as a technology for objectively measuring the refraction data of an eye, correction factors such as S (spherical power), C (astigmatic power), and A (angle of an astigmatic axis) are measured by the use of a refractometer. In recent years, eye-characteristics measurement apparatuses capable of measuring even higher-order aberration have been developed, and therefore, correction factors such as S, C, and A on a line such as a ring having a diameter of 3 mm used by a refractometer can be calculated from lower-order aberration. When such an eye-characteristics measurement apparatus is used, values closer to subjective values than those obtained by a refractometer are obtained especially for sick eyes and eyes on which refractive-power-correction operations have been performed. The following documents, for example, should be referenced.

Japanese Patent Application No. 2001-119145
Japanese Patent Application No. 2001-120002
Japanese Patent Application No. 2001-119086
Japanese Patent Application No. 2000-318534

DISCLOSURE OF INVENTION

However, there may occur differences between subjective values and the objective calculation results of conventional eye-characteristics measurement apparatuses, and insufficient evaluations may be obtained for correction factors such as S, C, and A.

FIG. 19 is a view showing a comparison between an objective examination and a subjective examination.

As shown in the figure, when the objective examination (objective refraction) and the subjective examination (subjective refraction) show the same results, the results are plotted on a line. In actual cases, however, the results of the examinations may have differences. Especially at a plot indicated by an arrow, there is a very large difference between the result of the objective examination, which is about −15, and the result of the subjective examination, which is about −7.5.

An object of the present invention is to obtain a result close to a subjective value by evaluating, for example, a human observer model from a measurement result obtained by an eye-characteristics measurement apparatus capable of measuring higher-order aberrations, not only when only higher-order aberrations, which correspond to a complete objective correction, are used but also when lower-order aberrations are added, by calculating, for example, a lower-order aberration amount which improves how an image is seen, and by obtaining data of correction factors such as S, C, and A at that time.

According to the first solving means of this invention, there is provided a correction-factor determination apparatus comprising:

an image-data generation section for performing simulation of how an eyesight-test-chart target is seen, according to measurement data which indicates at least the wavefront aberrations of an eye under measurement, with a correction factor for correcting refraction being taken into account, to generate target retina image data;

a correction-factor setting section for specifying a correction factor to be given to the image-data generation section; and a determination section for determining whether the specified correction factor is appropriate, according to corrected target retina image data generated by the image-data generation section and corrected by the correction factor specified by the correction-factor setting section, wherein the correction-factor setting section specifies the correction factor according to a result obtained by the determination section, and the correction-factor setting section changes the correction factor by the correction-factor setting section until the determination section determines that the correction factor is appropriate.

According to the second solving means of this invention, there is provided a correction-factor determination method including:

a step of generating target retina image data by performing simulation of how an eyesight-test-chart target is seen, according to measurement data which indicates at least the wavefront aberrations of an eye under measurement, with a correction factor for correcting refraction being taken into account;

a step of specifying a correction factor for generating the target retina image data; and a step of determining whether the specified correction factor is appropriate, according to corrected target retina image data generated in the step of generating the target retina image data and corrected by the correction factor specified in the step of specifying the correction factor, wherein the correction factor is specified in the step of specifying the correction factor, according to a result obtained in the step of determining, and the correction factor is changed in the step of specifying the correction factor until it is determined that the correction factor is appropriate in the step of determining.

According to the third solving means of this invention, there is provided a correction-factor determination method including:

a step of calculating which uses a first spherical power included in measurement data which indicates the refractive-power distribution of an eye under measurement, as a correction factor to calculate a second spherical power by the correction-factor determination method described above;

a step of obtaining the second spherical power from the second spherical power by compensating a value based on a first astigmatic power included in the measurement data which indicates the refractive-power distribution of the eye under measurement; and a step of calculating which uses the second spherical power as a correction factor to calculate a second astigmatic power by the correction-factor determination method described above.

BRIEF DESCRIPTION OF THE DRAWINGS

FIG. 3 is a view showing the Zernike coefficients of (r, t) coordinates.

FIG. 4 is a view showing the Zernike coefficients of (x, y) coordinates.

FIG. 9 is an explanatory view of template matching performed in step S407.

BEST MODE FOR CARRYING OUT THE INVENTION

1. Eye Optical Characteristic Measuring Apparatus

Figure 1:
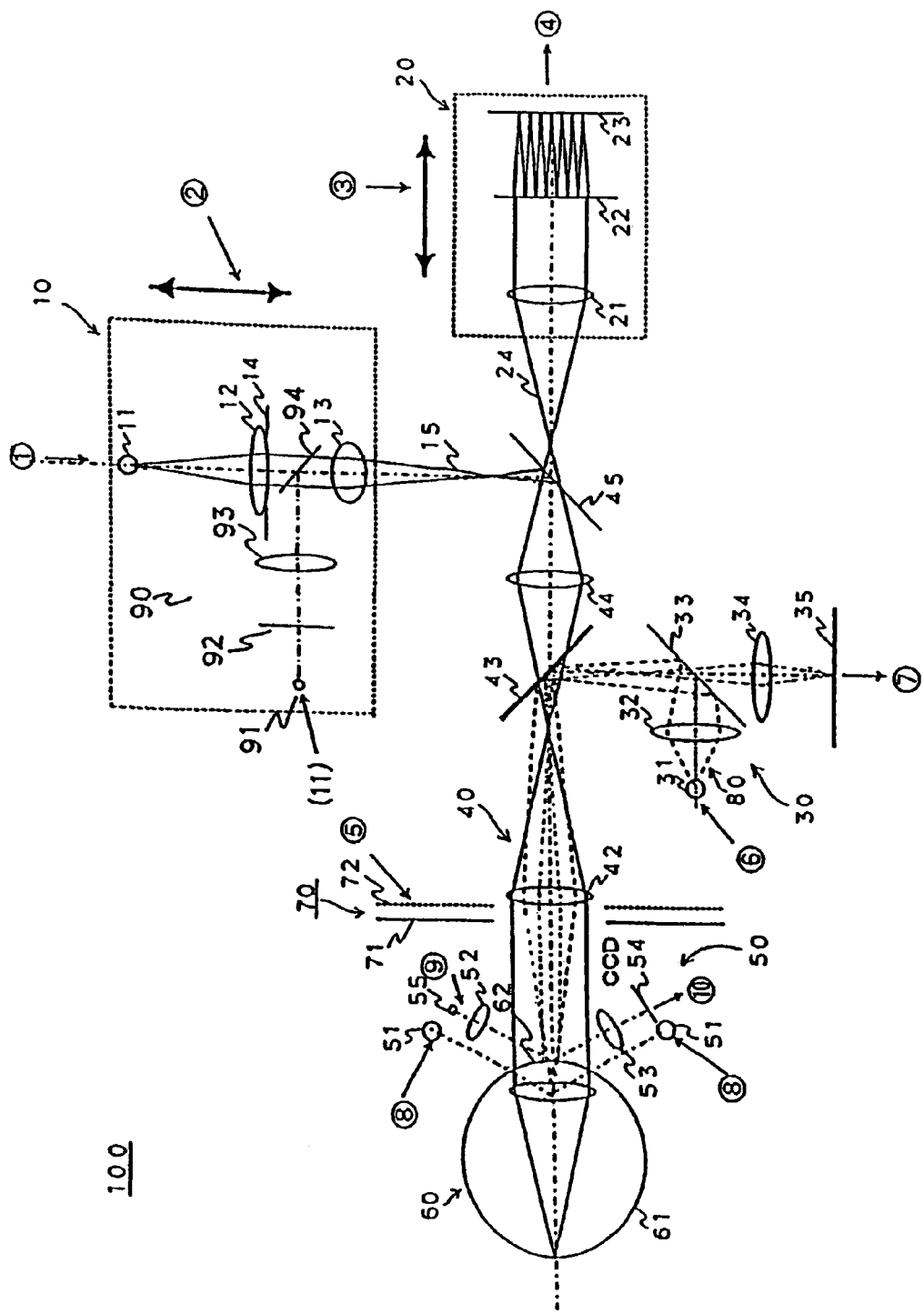
FIG. 1 is a structural view of an optical system 100 of an eye optical characteristic measuring apparatus.

FIG. 1 is a structural view of an optical system 100 of an eye optical characteristic measuring apparatus.

The optical system 100 of the eye optical characteristic measuring apparatus is an apparatus for measuring an optical characteristic of an eye 60 to be measured as an object, and includes a first illuminating optical system 10, a first light receiving optical system 20, a second light receiving optical system 30, a common optical system 40, an adjusting optical system 50, a second illuminating optical system 70, and a second light sending optical system 80. Incidentally, with respect to the eye 60 to be measured, a retina 61 and a cornea 62 are shown in the drawing.

The first illuminating optical system 10 includes, for example, a first light source part 11 for emitting a light flux of a first wavelength, and a condensing lens 12, and is for illuminating a minute area on the retina (retina) 61 of the eye 60 to be measured with the light flux from the first light source part 11 so that its illumination condition can be suitably set. Incidentally, here, as an example, the first wavelength of the illuminating light flux emitted from the first light source part 11 is a wavelength (for example, 780 nm) of an infrared range.

Besides, it is desirable that the first light source part 11 has a high spatial coherence and a low temporal coherence. Here, the first light source part 11 is, for example, a super luminescence diode (SLD), and a point light source having high luminescence can be obtained. Incidentally, the first light source part 11 is not limited to the SLD, and for example, a laser having a high spatial coherence and a high temporal coherence can also be used by inserting a rotation diffused plate or the like to suitably lower the temporal coherence. Further, an LED having a low spatial coherence and a low temporal coherence can also be used, if light quantity is sufficient, by inserting, for example, a pinhole or the like at a position of a light source in an optical path.

The first light receiving optical system 20 includes, for example, a collimator lens 21, a Hartmann plate 22 as a conversion member for converting a part of a light flux (first light flux) reflected and returned from the retina 61 of the eye 60 to be measured into at least 17 beams, and a first light receiving part 23 for receiving the plural beams converted by the Hartmann plate 22, and is for guiding the first light flux to the first light receiving part 23. Besides, here, a CCD with little readout noise is adopted for the first light receiving part 23, and as the CCD, a suitable type of CCD, for example, a general low noise type of CCD, a cooling CCD of 1000*1000 elements for measurement, or the like is applicable.

The second illuminating optical system 70 includes a second light source 72 and a Placido's disk 71. Incidentally, the second light source 72 can be omitted. The Placido's disk (PLACIDO'S DISK) 71 is for projecting an index of a pattern composed of plural co-axial rings. Incidentally, the index of the pattern composed of the plural co-axial rings is an example of an index of a specified pattern, and a different suitable pattern can be used. Then, after an alignment adjustment described later is completed, the index of the pattern composed of the plural co-axial rings can be projected.

The second light sending optical system 80 is for mainly performing, for example, the alignment adjustment described later, and measurement and adjustment of a coordinate origin and a coordinate axis, and includes a second light source part 31 for emitting a light flux of a second wavelength, a condensing lens 32, and a beam splitter 33.

The second light receiving optical system 30 includes a condensing lens 34 and a second light receiving part 35. The second light receiving optical system 30 guides a light flux (second light flux), which is originated from the pattern of the Placido's disk 71 illuminated from the second illuminating optical system 70 and is reflected and returned from the anterior eye part or the cornea 62 of the eye 60 to be measured, to the second light receiving part 35. Besides, it can also guide a light flux, which is emitted from the second light source part 31 and is reflected and returned from the cornea 62 of the eye 60 to be measured, to the second light receiving part 35. Incidentally, as the second wavelength of the light flux emitted from the second light source part 31, for example, a wavelength different from the first wavelength (here, 780 nm) and longer (for example, 940 nm) than that can be selected.

The common optical system 40 is disposed on an optical axis of the light flux emitted from the first illuminating optical system 10, can be included in the first and the second illuminating optical systems 10 and 70, the first and the second light receiving optical systems 20 and 30, the second light sending optical system 80 and the like in common, and includes, for example, an afocal lens 42, beam splitters 43 and 45, and a condensing lens 44. The beam splitter 43 is formed of such a mirror (for example, a dichroic mirror) that the wavelength of the second light source part 31 is sent (reflected) to the eye 60 to be measured, and the second light flux reflected and returned from the retina 61 of the eye 60 to be measured is reflected, and on the other hand, the wavelength of the first light source part 11 is transmitted.

The beam splitter 45 is formed of such a mirror (for example, a polarization beam splitter) that the light flux of the first light source part 11 is sent (reflected) to the eye 60 to be measured, and the first light flux reflected and returned from the retina 61 of the eye 60 to be measured is transmitted. By the beam splitters 43 and 45, the first and the second light fluxes do not mutually enter the other optical systems to generate noise.

The adjusting optical system 50 is for mainly performing, for example, a working distance adjustment described later, includes a third light source part 51, a fourth light source part 55, condensing lenses 52 and 53, and a third light receiving part 54, and is for mainly performing the working distance adjustment.

The third illuminating optical system 90 includes an optical path for projection of an index for causing, for example, fixation of the subject eye or fogging, and includes a fifth light source part (for example, a lamp) 91, a fixed index 92 and a relay lens 93. The fixed index 92 can be irradiated to the retina 61 by the light flux from the fifth light source part 91, and the subject eye 60 is made to observe its image. The fixed index 92 and the retina 61 are put in a conjugated relation by the third illuminating optical system 90.

Next, the alignment adjustment will be described. The alignment adjustment is mainly carried out by the second light receiving optical system 30 and the second light sending optical system 80.

First, the light flux from the second light source part 31 illuminates the eye 60 to be measured as the object with the substantially parallel light flux through the condensing lens 32, the beam splitters 33 and 43, and the afocal lens 42. The reflected light flux reflected by the cornea 62 of the eye 60 to be measured is emitted as a divergent light flux such as is emitted from a point at the half of the radius of curvature of the cornea 62. The divergence light flux is received as a spot image by the second light receiving part 35 through the afocal lens 42, the beam splitters 43 and 33, and the condensing lens 34.

Here, in the case where the spot image on the second light receiving part 35 is outside the optical axis, the main body of the eye optical characteristic measuring apparatus is moved and adjusted vertically and horizontally, and the spot image is made to coincide with the optical axis. As stated above, when the spot image coincides with the optical axis, the alignment adjustment is completed. Incidentally, with respect to the alignment adjustment, the cornea 62 of the eye 60 to be measured is illuminated by the third light source part 51, and an image of the eye 60 to be measured obtained by this illumination is formed on the second light receiving part 35, and accordingly, this image may be used to make the pupil center coincide with the optical axis.

Next, the working distance adjustment will be described. The working distance adjustment is mainly carried out by the adjusting optical system 50.

First, the working distance adjustment is carried out by, for example, irradiating the eye 60 to be measured with a parallel light flux emitted from the fourth light source part 55 and close to the optical axis, and by receiving the light reflected from the eye 60 to be measured through the condensing lenses 52 and 53 by the third light receiving part 54. Besides, in the case where the eye 60 to be measured is in a suitable working distance, a spot image from the fourth light source part 55 is formed on the optical axis of the third light receiving part 54. On the other hand, in the case where the eye 60 to be measured goes out of the suitable working distance, the spot image from the fourth light source part 55 is formed above or below the optical axis of the third light receiving part 54. Incidentally, since the third light receiving part 54 has only to be capable of detecting a change of a light flux position on the plane containing the fourth light source part 55, the optical axis and the third light receiving part 54, for example, a one-dimensional CCD arranged on this plane, a position sensing device (PSD) or the like is applicable.

Next, a positional relation between the first illuminating optical system 10 and the first light receiving optical system 20 will be described.

The beam splitter 45 is inserted in the first light receiving optical system 20, and by this beam splitter 45, the light from the first illuminating optical system 10 is sent to the eye 60 to be measured, and the reflected light from the eye 60 to be measured is transmitted. The first light receiving part 23 included in the first light receiving optical system 20 receives the light transmitted through the Hartmann plate 22 as the conversion member and generates a received light signal.

Besides, the first light source part 11 and the retina 61 of the eye 60 to be measured form a conjugated relation. The retina 61 of the eye 60 to be measured and the first light receiving part 23 are conjugate. Besides, the Hartmann plate 22 and the pupil of the eye 60 to be measured form a conjugated relation. Further, the front focal point of the afocal lens 42 is substantially coincident with the cornea 62 as the anterior eye part of the eye 60 to be measured and the pupil.

Besides, the first illuminating optical system 10 and the first light receiving optical system 20 are moved together so that a signal peak according to the reflected light at the light receiving part 23 becomes maximum on the condition that the light flux from the first light source part 11 is reflected at a point on which it is condensed. Specifically, the first illuminating optical system 10 and the first light receiving optical system 20 are moved in a direction in which the signal peak at the first light receiving part 23 becomes large, and are stopped at a position where the signal peak becomes maximum. By this, the light flux from the first light source part 11 is condensed on the eye 60 to be measured.

Besides, the lens 12 converts a diffused light of the light source 11 into a parallel light. A diaphragm 14 is positioned at an optically conjugated position with respect to the pupil of the eye or the Hartmann plate 22. The diaphragm 14 has a diameter smaller than an effective range of the Hartmann plate 22, and the so-called single path aberration measurement (method in which aberrations of an eye have an influence on only the light receiving side) is established. In order to satisfy the above, the lens 13 is disposed such that the retina conjugated point of the real light beam coincides with the front focal position, and further, in order to satisfy the conjugated relation between the lens and the pupil of the eye, it is disposed such that the rear focal position coincides with the diaphragm 14.

Besides, after a light beam 15 comes to have a light path common to a light beam 24 by the beam splitter 45, it travels in the same way as the light beam 24 paraxially. However, in the single path measurement, the diameters of the light beams are different from each other, and the beam diameter of the light beam 15 is set to be rather small as compared with the light beam 24. Specifically, the beam diameter of the light beam 15 is, for example, about 1 mm at the pupil position of the eye, and the beam diameter of the light beam 24 can be about 7 mm (incidentally, in the drawing, the light beam 15 from the beam splitter 45 to the retina 61 is omitted).

Next, the Hartmann plate 22 as the conversion member will be described.

The Hartmann plate 22 included in the first light receiving optical system 20 is a wavefront conversion member for converting a reflected light flux into plural beams. Here, plural micro-Fresnel lenses disposed on a plane orthogonal to the optical axis apply in the Hartmann plate 22. Besides, in general, with respect to the measurement object part (the eye 60 to be measured), in order to measure a sphere of the eye 60 to be measured, third-order astigmatism aberrations, and other higher order aberrations, it is necessary to perform the measurement with at least 17 beams through the eye 60 to be measured.

Besides, the micro-Fresnel lens is an optical element, and includes, for example, a ring with a height pitch for each wavelength, and a blade optimized for emission parallel to a condensing point. The micro-Fresnel lens here is subjected to, for example, 8-level optical path length variation employing a semiconductor fine working technique, and achieves a high condensing efficiency (for example, 98%).

Besides, the reflected light from the retina 61 of the eye 60 to be measured passes through the afocal lens 42 and the collimate lens 21 and is condensed on the first light receiving part 23 through the Hartmann plate 22. Accordingly, the Hartmann plate 22 includes a wavefront conversion member for converting the reflected light flux into at least 17 beams.

Figure 2:
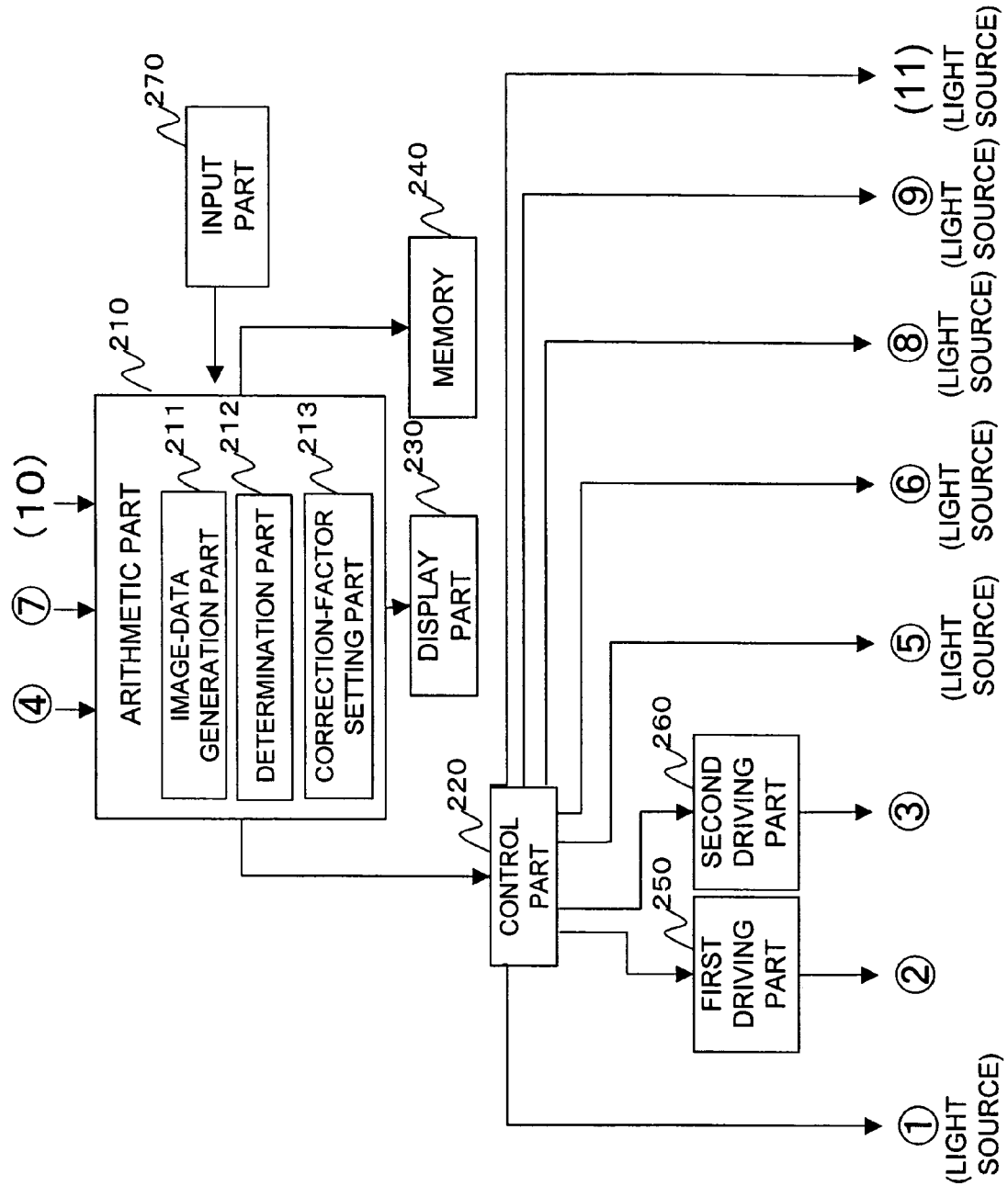
FIG. 2 is a structural view of an electrical system 200 of the eye optical characteristic measuring apparatus.

FIG. 2 is a structural view of an electrical system 200 of the eye optical characteristic measuring apparatus. The electrical system 200 of the eye optical characteristic measuring apparatus includes, for example, an arithmetic part 210, a control part 220, a display part 230, a memory 240, a first driving part 250, a second driving part 260, and an input part 270. The arithmetic part 210 has an image-data generation part 211, a correction-factor setting part 213, and a determination part 212.

The arithmetic part 210 receives a received-light signal (4) obtained from the first light receiving part 23, a received-light signal (7) obtained from the second light receiving part 35, and a received-light signal (10) obtained from the third light receiving part 54, and performs calculations for the origin of coordinates, a coordinate axis, changes in coordinates, rotation, total wavefront aberrations, corneal wavefront aberrations, Zernike coefficients, aberration coefficients, a Strehl ratio, a white-light MTF, a Landolt's ring pattern, and others. The arithmetic part 210 also outputs signals corresponding to such calculation results to the control part 220, which controls the entire electric driving system, to the display part 230, and to the memory 240. Details of the operation of the arithmetic part 210 will be described later.

The image-data generation part 211 simulates how an eyesight test chart target is seen according to measurement data which indicates at least the wavefront aberrations of an eye under examination, with a correction factor for refraction correction being taken into account, to generate target retina image data. The wavefront aberrations of the eye under examination includes higher-order aberrations. The correction-factor setting part 213 specifies a correction factor to be given to the image-data generation part 211. The determination part 212 determines whether the correction factor is appropriate according to corrected target retina image data corrected by the correction factor specified by the correction-factor setting part 213 and generated by the image-data generation part 211. The correction-factor setting part 213 sets the correction factor according to the result of the determination part 212, and repeatedly changes the correction factor until the determination part 212 determines that the correction factor is appropriate. The correction factor includes one of a spherical power, an astigmatic power, and the angle of an astigmatic axis, or a combination of two or three thereof.

It is possible that the correction-factor setting part 213 is configured so as to change the correction factor in the order of the spherical power, the angle of the astigmatic axis, and the astigmatic power, and the determination part 212 is configured so as to determine whether an appropriate correction factor has been set in the order of the spherical power, the angle of the astigmatic axis, and the astigmatic power. When the spherical power and/or the astigmatic power is selected as the correction factor, the image-data generation part 211 can sequentially switch the eyesight test chart target with which the simulation is performed to eyesight test chart targets having different sizes to simulate how the target is seen to generate target retina image data. When it is determined whether the spherical power or the astigmatic power is appropriate, the eyesight test chart target with which the image-data generation part 211 performs the simulation can, for example, be a Landolt's ring target. A letter target or a natural image may be effective in some cases. A contrast target may be used.

The determination part 212 can be configured so as to compare matching pattern data of a certain eyesight test chart target with the target retina image data obtained in the simulation to obtain the degree of correlation to determine whether the correction factor is appropriate. In this case, the determination part 212 can, for example, apply two-dimensional Fourier transform to the spatial frequency of a template and multiply the resultant by the spatial-frequency distribution of an retina image to perform determination by template matching. The image-data generation part 211 can be configured so as to calculate a pupil function from the wavefront aberrations, to calculate the luminance distribution function of a visual-acuity target, to multiply the function by the spatial-frequency distribution of the eye, and to apply two-dimensional inverse Fourier transform to the resultant to obtain target retina image data obtained by simulating measurement data indicating the refractive-power distribution of the eye under measurement, and/or the target retina image data corrected by the specified correction factor.

It is also possible that the image-data generation part 211 is configured so as to generate MTF data as the simulation of how the eyesight test chart target is seen, with measurement data indicating at least the wavefront aberrations of the eye under measurement and a correction factor for refraction correction being taken into account, and the determination part 212 is configured so as to determine according to the generated MTF data whether the correction factor is appropriate.

The correction-factor setting part 213 can be configured so as to perform correction from a weak correction point in usual cases. The correction-factor setting part 213 can also be configured so as to perform correction according to a subjective-measurement procedure.

The control part 220 controls lighting and extinction of the first light source part 11 on the basis of the control signal from the arithmetic part 210, or controls the first driving part 250 and the second driving part 260. For example, on the basis of the signals corresponding to the operation results in the arithmetic part 210, the control part outputs a signal (1) to the first light source part 11, outputs a signal (5) to the Placido's disk 71, outputs a signal (6) to the second light source part 31, outputs a signal (8) to the third light source part 51, outputs a signal (9) to the fourth light source part 55, outputs a signal (11) to the fifth light source part 91, and outputs signals to the first driving part 250 and the second driving part 260.

The first driving part 250 is for moving the whole first illuminating optical system 10 in the optical axis direction on the basis of, for example, the received light signal (4) inputted to the arithmetic part 210 from the first light receiving part 23, and outputs a signal (2) to a not-shown suitable lens movement means and drives the lens movement means. By this, the first driving part 250 can perform the movement and adjustment of the first illuminating optical system 10.

The second driving part 260 is for moving the whole first light receiving optical system 20 in the optical axis direction on the basis of, for example, the received light signal (4) inputted to the arithmetic part 210 from the first light receiving part 23, and outputs a signal (3) to a not-shown suitable lens movement means, and drives the lens movement means. By this, the second driving part 260 can perform the movement and adjustment of the first light receiving optical system 20.

2. Zernike Analysis

Next, a Zernike analysis will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 23 through the Hartmann plate 22.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate 22.

Besides, with respect to the wavefront aberrations W(X, Y), when the horizontal and vertical coordinates of the first light receiving part 23 are denoted by (x, y), a distance between the Hartmann plate 22 and the first light receiving part 23 is denoted by f, and a movement distance of a point image received by the first light receiving part 23 is denoted by (Δx, Δy), the following expression is established.

$$\frac{\partial W(X, Y)}{\partial X} = \frac{\Delta x}{f}$$

$$\frac{\partial W(X, Y)}{\partial Y} = \frac{\Delta y}{f}$$

Where, the Zernike polynomials $Z_i^{2j-i}$ are expressed by the following numerical expressions.

FIG. 3 is a view of the Zernike coefficients of (r, t) coordinates, and FIG. 4 is a view of the Zernike coefficients of (x, y) coordinates. Specifically, Zernike polynomials $Z_i^{2j-i}$ are expressed by these figures.

$$Z_n^m = R_n^m(r) \left\{ \begin{array}{c} \sin \\ \cos \end{array} \right\} \{m\theta\}$$

-continued $m > 0$ sin $m \leq 0$ cos $$R_n^m(r) = \sum_{S=0}^{(n-m)/2} (-1)^S \frac{(n-S)!}{S!\left\{\frac{1}{2}(n-m)-S\right\}!\left\{\frac{1}{2}(n+m)-S\right\}!} r^m$$

Incidentally, with respect to the Zernike coefficients $C_i^{2j-i}$, specific values can be obtained by minimizing the squared error expressed by the following numerical expression.

$$S(x) = \sum_{i=1}^{data\_number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right]$$

Where, W(X, Y): wavefront aberrations, (X, Y): Hartmann plate coordinates, (Δx, Δy): a movement distance of a point image received by the first light receiving part 23, f: a distance between the Hartmann plate 22 and the first light receiving part 23, m: the number of data.

The arithmetic part 210 calculates the Zernike coefficients $C_i^{2j-i}$, and uses this to obtain eye optical characteristics such as spherical aberrations, coma aberrations, and astigmatism aberrations. The arithmetic part 210 calculates a spherical power of the eye to be measured based on a moving amount of the first light receiving optical system and the wavefront aberrations.

3. Landolt's Ring

Figure 5:
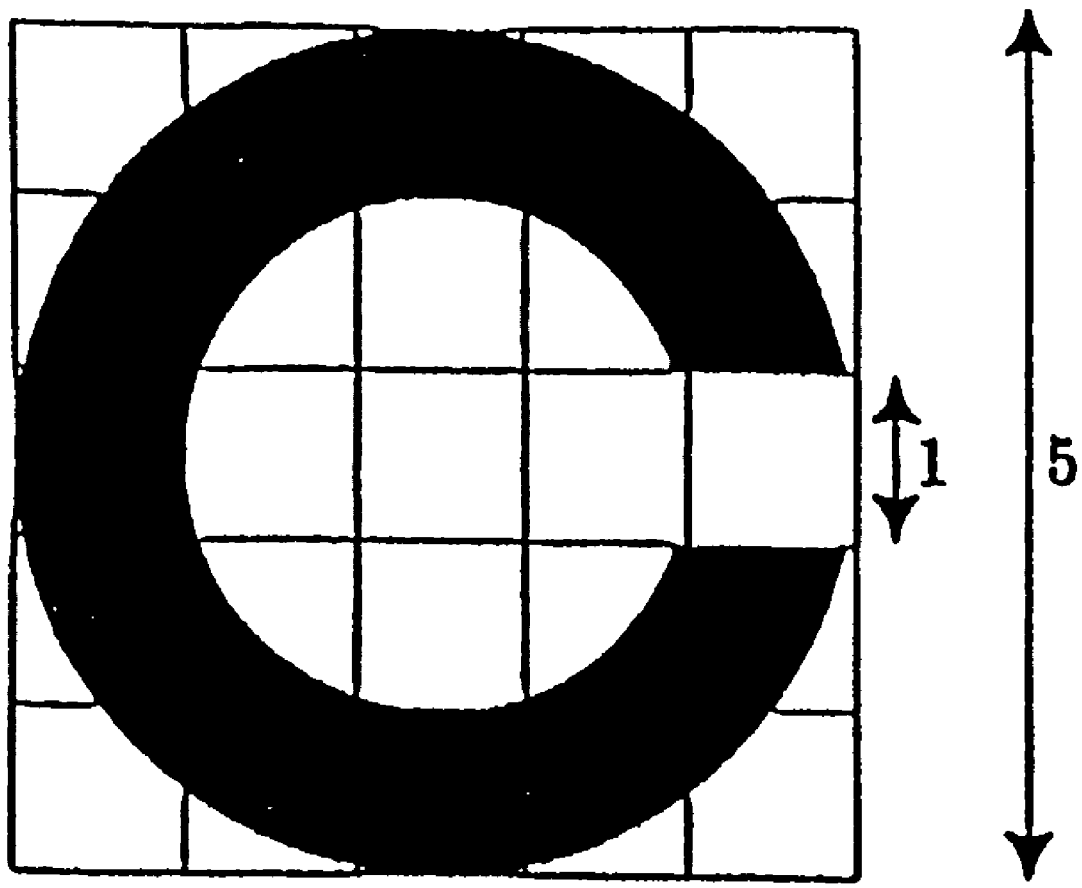
FIG. 5 is an explanatory view of a Landolt's ring.

FIG. 5 is an explanatory view of a Landolt's ring.

Hereinafter, preparation of data of a luminous distribution function Land(x, y) of the Landolt's ring will be described.

The Landolt's ring is expressed by the reciprocal of a recognizable minimum visual angle, and the ability to be capable of recognizing a visual angle of one minute is called visual acuity of 20/20. For example, if the recognizable minimum visual angle is 2 minutes, the visual acuity is defined as 20/40, and if 10 minutes, the visual acuity is defined as 20/200. In general, the Landolt's ring uses, as an index, a ring in which a gap being ⅕ of the size of the outside ring is provided as shown in the drawing.

When the visual acuity is V, the size d of the Landolt's ring projected on the retina is calculated by $$d = 5 \times 2 \cdot R \tan\left(\frac{1}{60 \cdot V} \times \frac{1}{2}\right)$$

(R: a distance between a pupil and an image point (retina))

On the basis of this expression and the definition of the Landolt's ring, a black portion of the Landolt's ring is made 0, a white portion thereof is made 1, and the luminous distribution function Land(x, y) of the Landolt's ring is prepared. The data of the prepared luminous distribution function Land(x, y) is stored in the memory 240, is read out by the arithmetic part 210, and is set correspondingly to predetermined visual acuity.

4. Correction-Factor Determination Method (First Embodiment)

Figure 6:
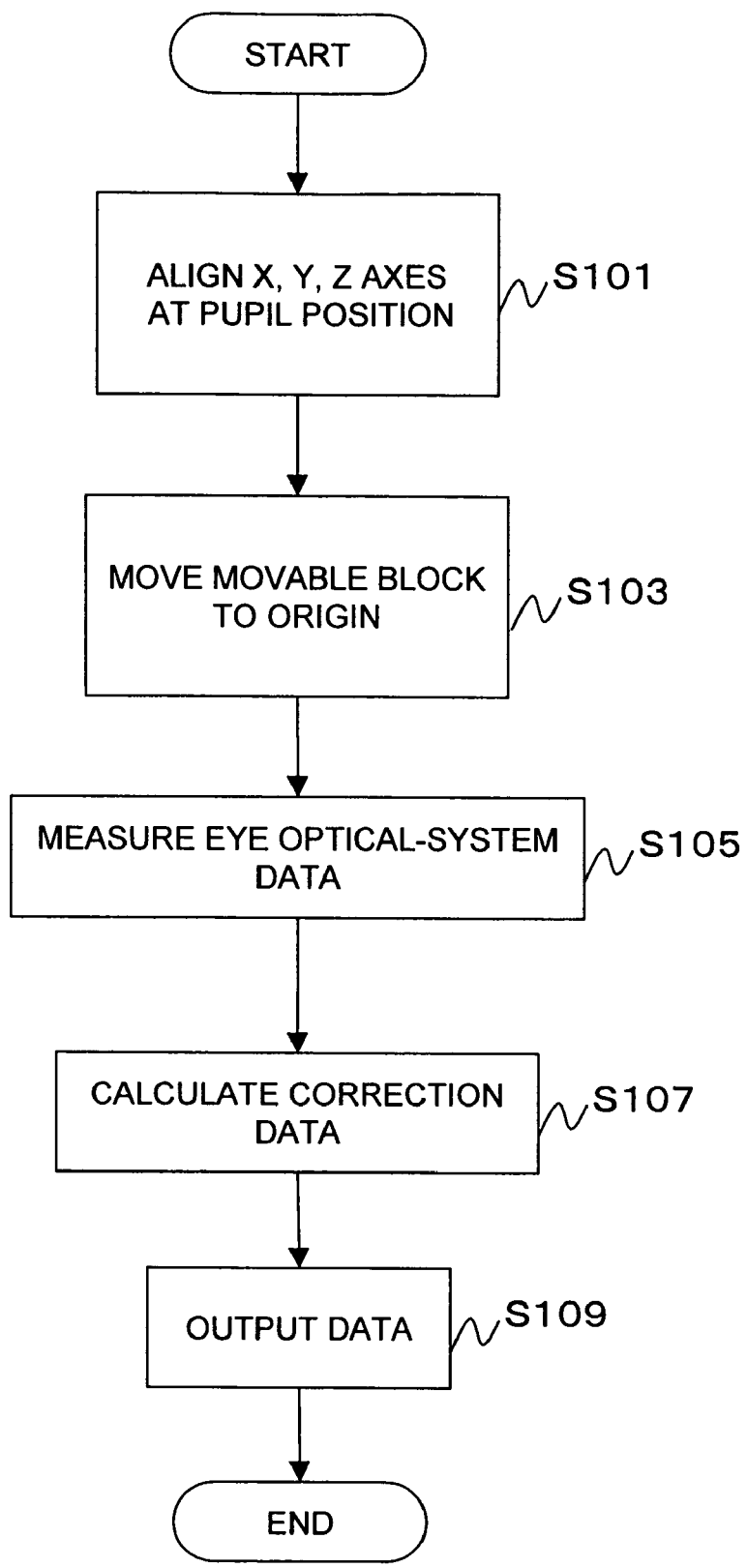
FIG. 6 is a flowchart of a correction-factor determination method according to a first embodiment.

FIG. 6 is a flowchart of a correction-factor determination method according to a first embodiment.

The eye-characteristic measuring apparatus first aligns the X, Y, and Z axes at the pupil position of the eye under measurement (S101). The measuring apparatus next moves the movable block to its origin (S103). For example, the Hartmann plate and the Placido's ring are adjusted to a diopter of zero. The arithmetic part 210 measures eye optical-system data such as the total wavefront aberrations and the Zernike coefficients according to the measured received-light signals ④, ⑦, and/or (10) (S105). The arithmetic part 210 simulates how the eyesight test chart target is seen and generates target retina image data to calculate correction data (correction factor) (S107). The correction factor includes one of the spherical power (S), the astigmatic power (C), and the angle (A) of the astigmatic axis, or a combination of two or three thereof. Details of this processing will be described later. The arithmetic part 10 outputs the correction factor, image simulation data corrected with the correction factor, and others to the display part 230 and to the memory 240 (S109).

A specific display example will be described below.

When a correction value is obtained by the above-described method, visual-acuity-chart simulation can be performed according to a spherical power, an astigmatic power, and the angle of an astigmatic axis serving as correction means and input, for example, through a user interface such as a dialog box, and a measured spherical power (the diopter value when de-focused is equal to the measured spherical power minus the spherical power serving as correction means), a measured astigmatic power, a measured angle (astigmatic contribution to wavefront aberrations in simulation is equal to wavefront aberrations caused by a measured astigmatic amount minus wavefront aberrations caused by an astigmatic amount serving as correction means) of the astigmatic axis, and higher-order aberrations, and the simulation result can be displayed.

In this simulation, not only the original target image used for estimating the correction value but also Landolt's rings having different powers and other letter targets such as the whole Snellen letter target can be used. In order for the user to use a desired target or a target similar thereto as the original image for simulation, simulation can be applied to a target image desired by the user and input with a scanner, input image data such as bitmap data, or data input to a target drawn by using a drawing program or a mechanical-design CAD program, and the simulation result can be displayed. A natural image is a part of desired targets.

Figure 20:
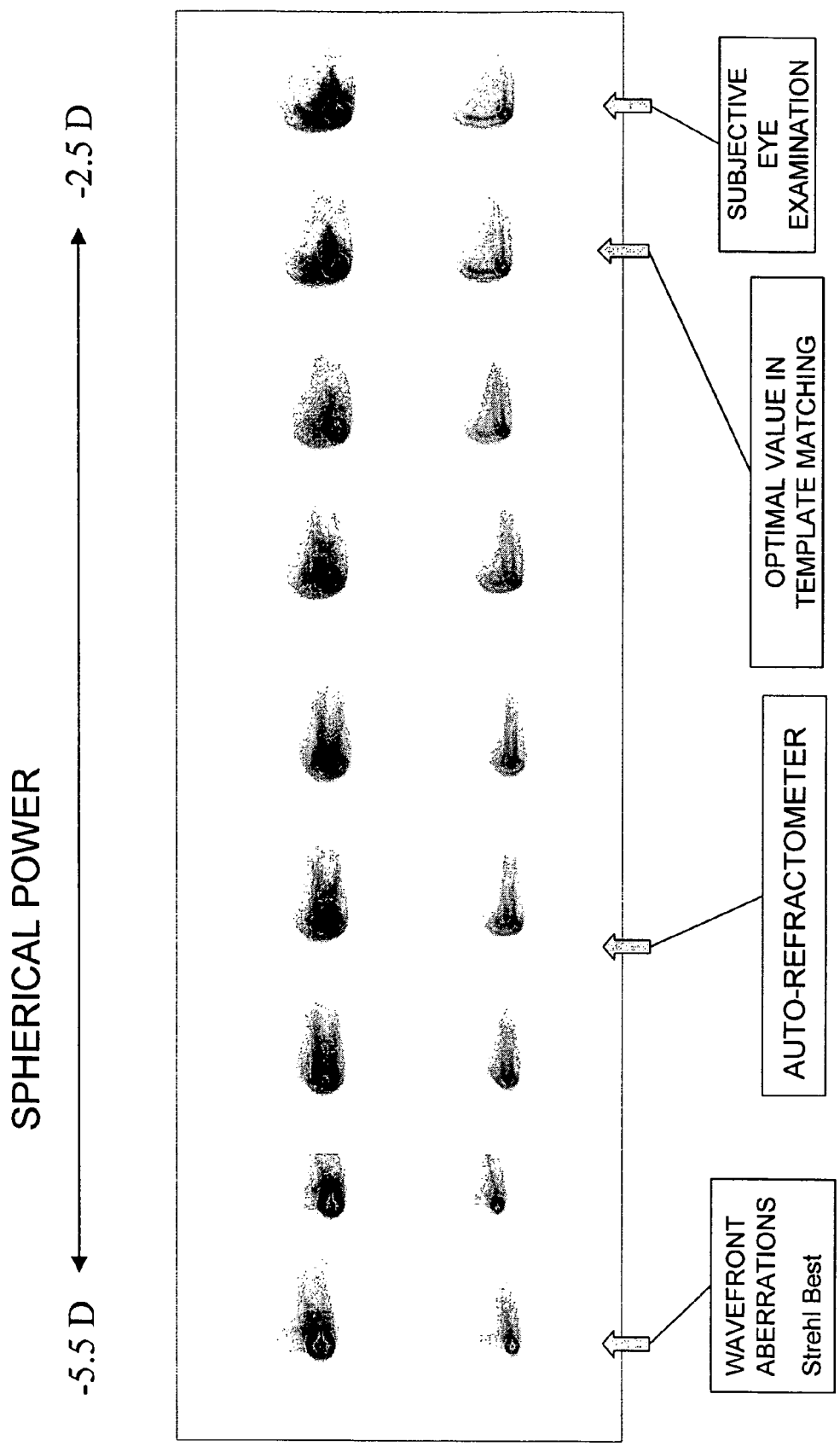
FIG. 20 is a view showing an example display of a simulation result.

In a display example of a simulation result, as shown in FIG. 20, target retina images obtained by simulation are displayed which uses a correction factor which makes best the Strehl ratio based on a measurement for the wavefront aberrations of the eye under measurement, a correction factor obtained by a result of an auto-refractometer measurement, a correction factor obtained by subjective eyesight examination and input if necessary, and correction data obtained by the processing described in the present embodiment. The display area shown in FIG. 20 includes all of various correction factors, but a display area which includes some of the correction factors may be used. The display area can also be specified by inputting one of the spherical power, the astigmatic power, and the angle of the astigmatism axis with its range. This function is very useful for research on presbyopia and adjustment functions because the function can be used for final confirmation and can also make definite what kind of optical characteristics the eye has in a depth direction.

Figure 21:
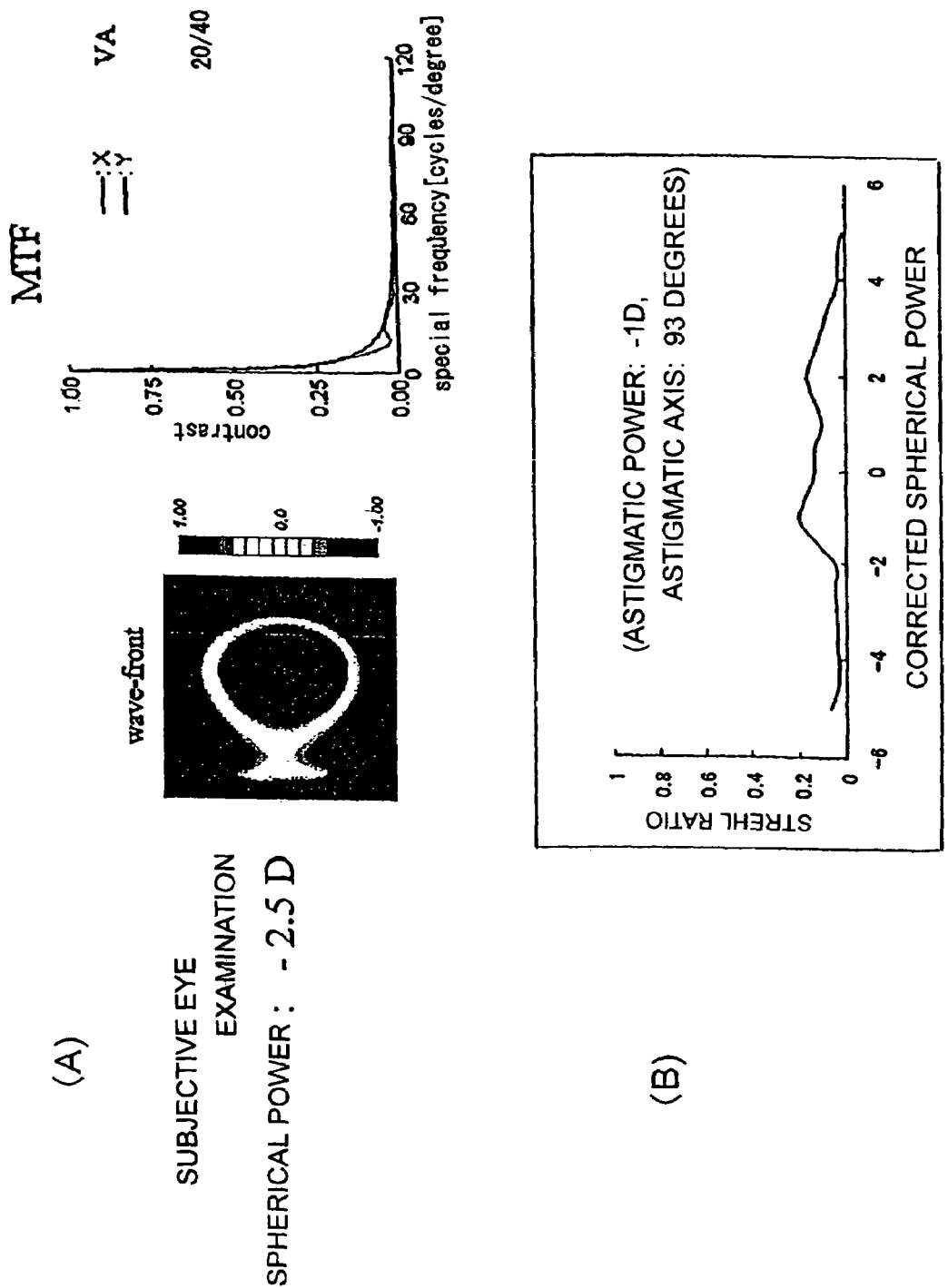
FIG. 21 is a view showing an example display which includes an MTF, a Strehl ratio, and others.

The display can be applied not only to retina-image simulation but also to a spatial-frequency characteristic (MTF) and a point spread function (PSF) (FIG. 21(A)). MTF at a specified spatial frequency, the Strehl ratio of the point spread function, or others can be output, for example, in a range where the spherical power has been input (FIG. 21(B)).

4-1. Correction Data Calculation (Spherical Power-1)

Figure 7:
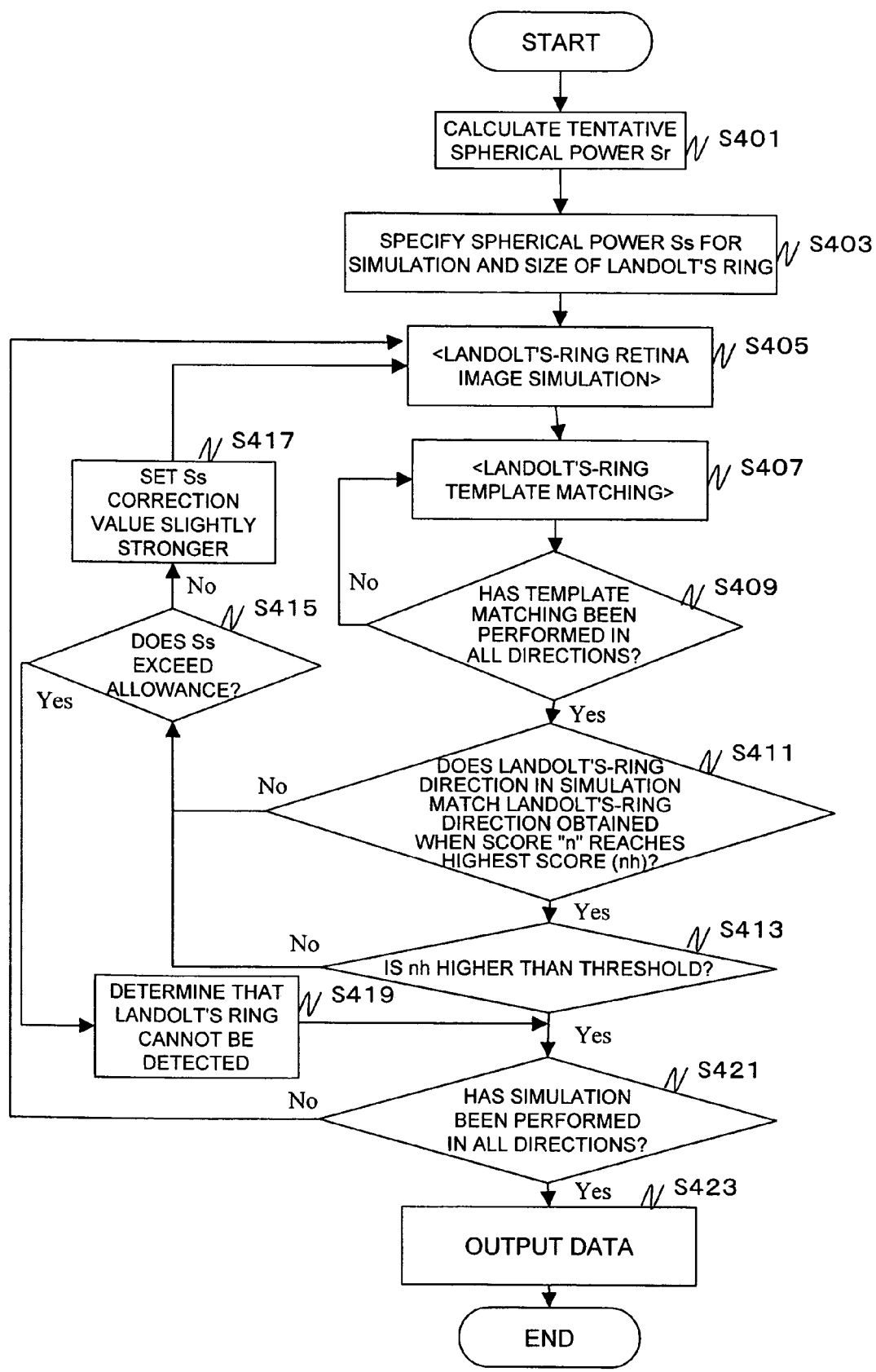
FIG. 7 is a flowchart of correction-data calculation (spherical power-1).

FIG. 7 is a flowchart of correction-data calculation (spherical power-1).

The arithmetic part 210 calculates a tentative spherical power Sr (S401). As the spherical power Sr, a refractive power or a value calculated from the wavefront aberrations may be used, for example. Alternatively, a value stored in the memory 240 in advance or a value input from the input part may also be used.

Then, the arithmetic part 210 specifies a spherical power Ss used in simulation, and the size of a Landolt's ring (S403). Usually, Ss is set weaker in correction (more near-sighted as a result) than Sr (for example, Ss=Sr+5D). For example, the size of a Landolt's ring can be calculated from Sr, if necessary, or it is possible that a correspondence table having stored Sr, other correction factors, or Zernike coefficients and corresponding visual acuity is stored in the memory 240 in advance and the arithmetic part 210 references it to determine the size of a Landolt's ring.

Then, the image-data generation part 211 of the arithmetic part 210 performs Landolt's-ring retina image simulation to obtain target retina image data (S405). The image-data generation part 211 first applies simulation to the Landolt's ring in a direction specified in advance (such as a ring having an opening in the upper, lower, right, or left direction). More specifically, the image-data generation part 211 obtains target retina image data which indicates how the Landolt's ring is seen, by simulation according to the wavefront aberrations measured in step S105. Specific simulation processing will be described later.

Next, the determination part 212 of the arithmetic part 210 performs Landolt's-ring template matching (S407). The determination part 212 performs template matching between the target retina image data obtained by the simulation and the Landolt's ring in a certain direction, and stores the direction and a score "n" which indicates the matching degree in the memory 240. A specific process will be described later.

The determination part 212 determines (S409) whether template matching has been performed in all directions of the Landolt's ring template. If no, the processing proceeds to step S407, and the matching process is repeated until template matching has been performed in all directions. When yes in step S409, the determination part 212 determines (411) whether the direction of the opening of the Landolt's ring used when the highest score nh is obtained matches the direction of the opening of the Landolt's ring of the target retina image data in the simulation. If yes, the determination part 212 determines (S413) whether the score nh is higher than a threshold specified in advance in the memory 240 or others.

If no in step S411 or step S413, the determination part 212 determines (S415) whether Ss exceeds an allowance (for example, Sr−5D) specified in advance. If no, the correction-factor setting part 213 sets the Ss correction factor slightly stronger (for example, Ss=Ss−0.25D) (S417), and the image-data generation part 211 performs Landolt's-ring retina image simulation according to this correction factor. The processes of step S407 and subsequent steps are executed for the target retina image data obtained by the simulation. When yes is step S415, the determination part 212 determines (S419) that the Landolt's ring cannot be detected, and stores the direction and the fact that the Landolt's ring cannot be detected in the direction, in the memory 240.

After step S419, or when yes in step S413, the determination part 212 determines (S421) whether simulation has been performed in all directions of the simulation Landolt's ring. If no, the processing returns to step S405, and the arithmetic part 210 repeats the above-described processes in all directions. When yes in step S421, the arithmetic part 210 outputs data (S423). More specifically, the arithmetic part 210 displays, for example, the spherical power S=Ss, the direction of the Landolt's ring which could be detected, the size of the Landolt's ring, simulation results, and others on the display part 230, and stores them in the memory 240.

(Retina Image Simulation)

Figure 8:
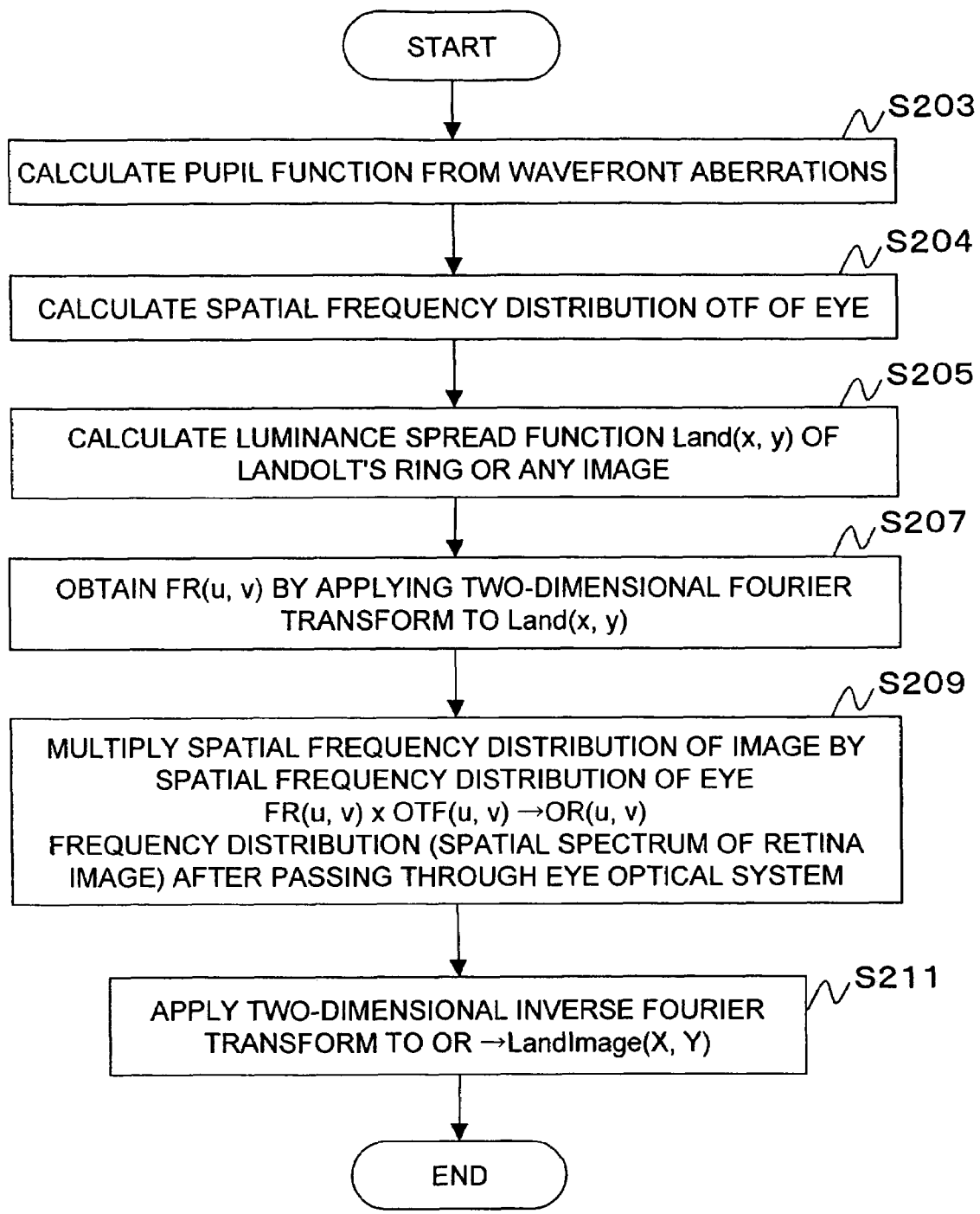
FIG. 8 is a flowchart of retina-image simulation performed in step S405.

FIG. 8 is a flowchart of the retina image simulation performed in step S405 described above.

The arithmetic part 210 calculates a pupil function f(x, y) by the following expression (S203) from the wavefront aberrations W(x, y) obtained in step S105.

$$W(X, Y) = \sum_{i=0}^{n} \sum_{j=0}^{i} c_i^{2j-i} Z_i^{2j-i}(X, Y)$$

$$f(x, y) = e^{ikW(x,y)}$$

where i indicates an imaginary number, k indicates a wave vector of $2\pi/\lambda$, and $\lambda$ indicates a wavelength.

Next, the spatial frequency distribution OTF of the eye is obtained in step S204. The arithmetic part 210 applies the Fourier transform to the pupil function f(x, y) to obtain the point spread function U(u, v) by amplitude as in the following expression.

$$U(u, v) = \int\int_{-\infty}^{\infty} f(x, y) \exp\left[-\frac{i}{R}\frac{2\pi}{\lambda}(ux+vy)\right] dxdy$$

where, $\lambda$ indicates a wavelength, R indicates the distance from the pupil to the image point (retina), (u, v) indicates coordinates in the plane perpendicular to the optical axis and having the image point O as the origin, and (x, y) indicates coordinates in the pupil plane.

The arithmetic part 210 multiplies U(u, v) by its complex conjugate to obtain the point spread function (PSF) I(u, v) by the following expression.

I(u, v)=U(u, v)U*(u, v)

Then, the arithmetic part 210 applies the Fourier transform (or self correlation) to PSF to standardize it to obtain OTF as in the following expression.

$$R(r, s) = \int\int_{-\infty}^{\infty} I(u, v)e^{-2\pi(ru+sv)} dudv$$

(r, s: variable of spatial frequency field)

$$OTF = \frac{R(r, s)}{R(0, 0)}$$

The arithmetic part 210 calculates the luminance spread function Land(x, y) of the Landolt's ring (or any image) by referring to the memory 240 (s205). The arithmetic part 210 applies two-dimensional Fourier transform to Land(x, y) to obtain the spatial frequency distribution FR(u, v) (S207). The arithmetic part 210 multiplies the spatial frequency distribution FR(u, v) of the Landolt's ring (or any image) by the spatial frequency distribution OTF of the eye, as in the following expression to obtain the frequency distribution OR(u, v) after passing through the eye optical system (S209).

FR(u, v)×OTF(u, v) - - - >OR(u, v)

Next, the arithmetic part 210 applies two-dimensional inverse Fourier transform to OR(u, v) to obtain the luminance spread image LandImage(X, Y) of the Landolt's ring (or any image) (S211). The arithmetic part 210 appropriately displays LandImage(X, Y), PSF(X, Y), and others on the display part 230 by an appropriate method, such as by figures, graphic data, graphs, and/or numerals, and appropriately stores the data in the memory 240.

(Template Matching)

FIG. 9 shows an explanatory view indicating the template matching performed in step S407 described above.

As shown in the figure, a template image (lower image) is specified correspondingly to the original Landolt's ring image (upper image), and the template image is stored in association with an identifier indicating the size of the Landolt's ring, in the memory 240. In this example, in the template image, b=1.5a, the number of pixels at a Landolt's-ring block is set to N1, their pixel value is set to 1, the number of pixels at a blurred-point-image block around the Landolt's-ring block is set to N2, and their pixel value is set to −N1/N2. The template image is not limited to this example, and can be appropriately specified.

Figure 10:
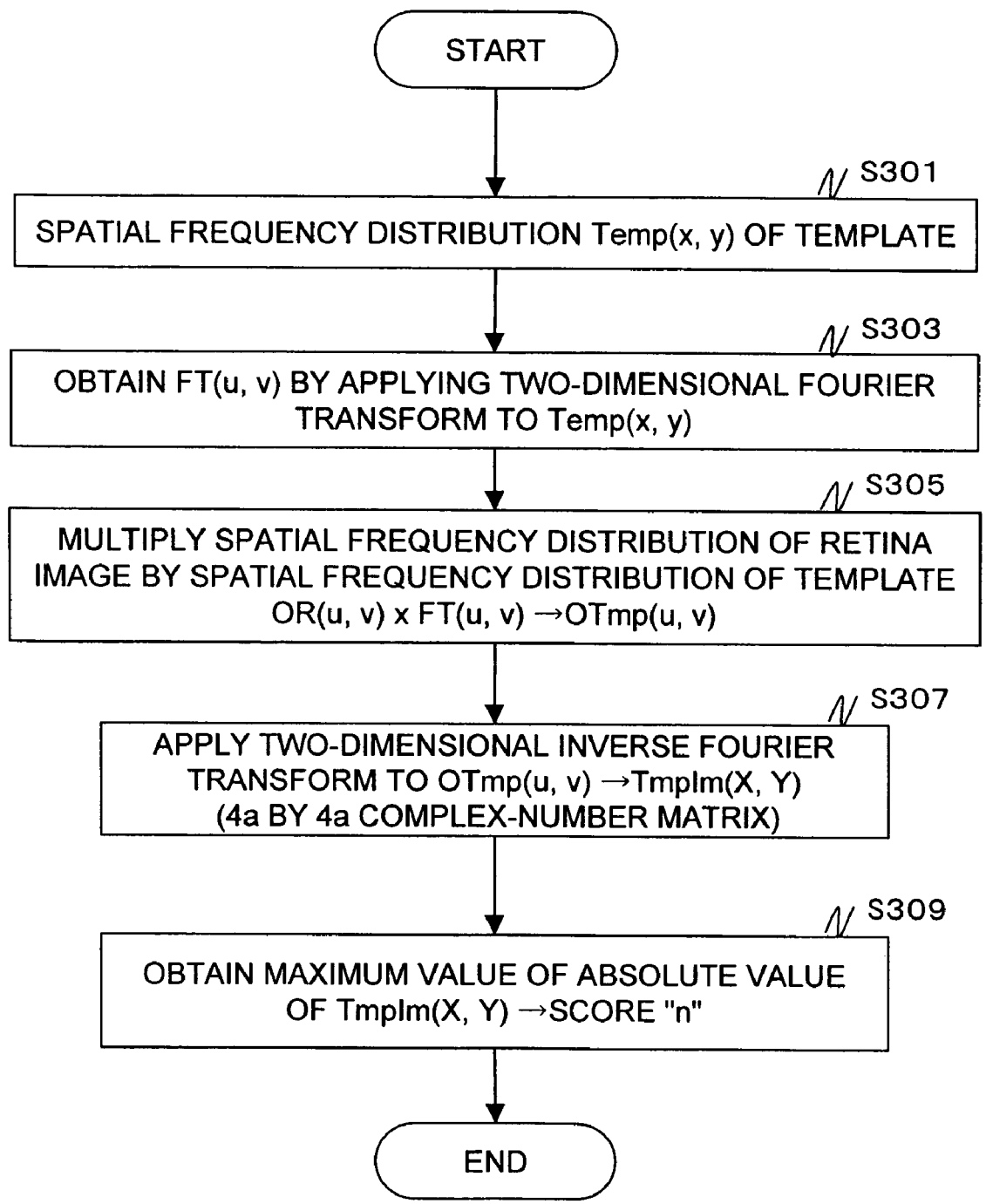
FIG. 10 is a flowchart of the template matching.

FIG. 10 is a flowchart of the template matching.

The arithmetic part 210 reads the template image according to the specified size of the Landolt's ring from the memory 240, and obtains its spatial frequency distribution Temp(x, y) (S301). Then, the arithmetic part 210 applies two-dimensional Fourier transform to Temp(x, y) to obtain FT(u, v) (S303). The arithmetic part 210 applies two-dimensional Fourier transform to the spatial frequency distribution of the target retina image data obtained by retina-image simulation to obtain OR(u, v), and multiplies OR(u, v) by the spatial frequency distribution FT(u, v) of the template, as in the following expression, to obtain OTmp(u, v) (S305).

OR(u, v)×FT(u, v) - - - >OTmp(u, v)

The arithmetic part 210 applies two-dimensional inverse Fourier transform to OTmp(u, v) to obtain TmpIm(X, Y) (4a by 4a complex-number matrix) (S307). The arithmetic part 210 obtains the maximum value of the absolute values of TmpIm(X, Y), and sets it as a score "n" (S309).

With such correlation, when the simulation target image is close to the original image, a high score is obtained. If the simulation target image is blurred, the score becomes lower accordingly.

4-2. Correction Data Calculation (Spherical Power-2)

Figure 11:
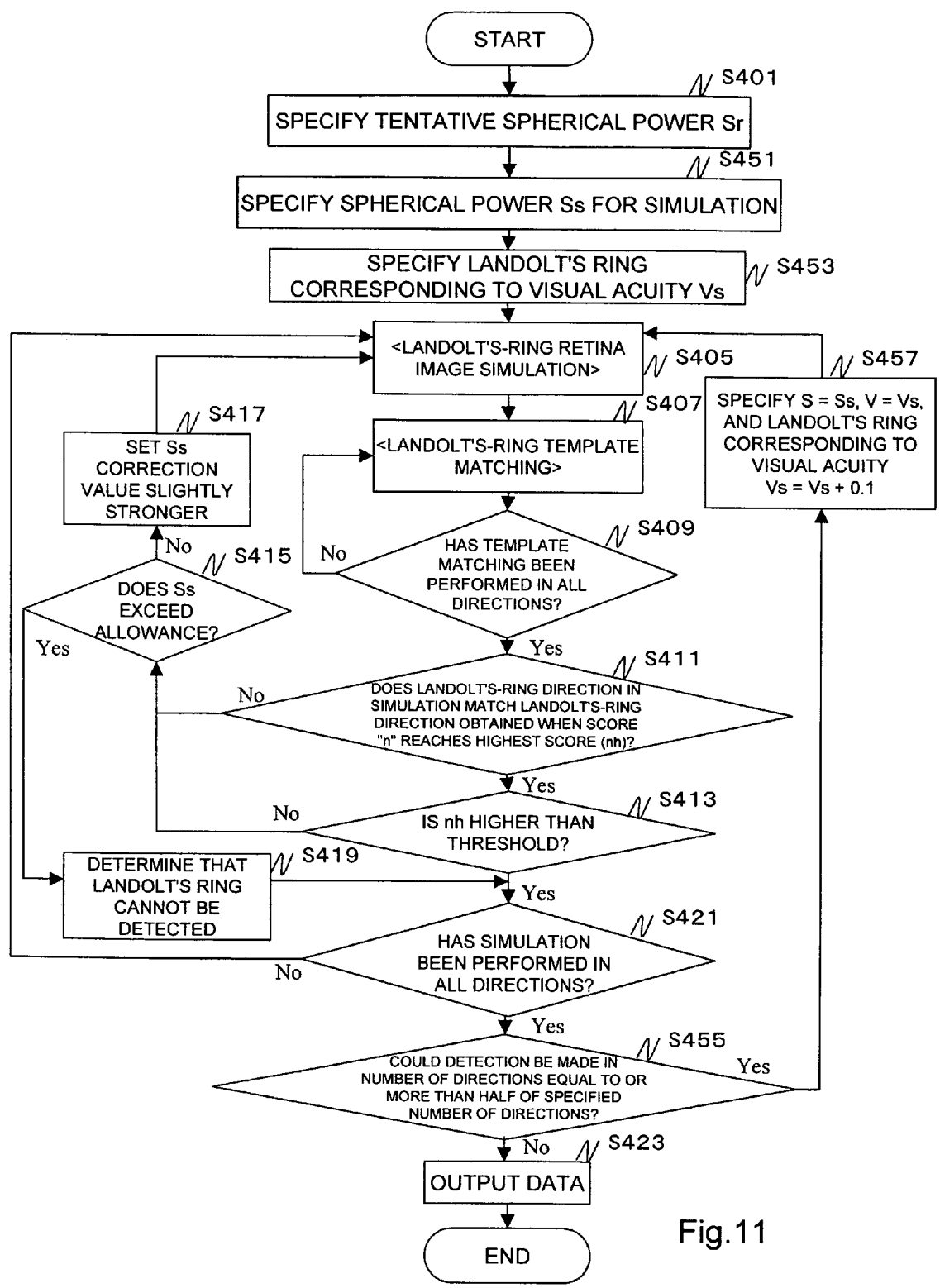
FIG. 11 is a flowchart of correction-data calculation (spherical power-2).

FIG. 11 is a flowchart of correction-data calculation (spherical power-2). In each of the following flow charts, the same processes are executed in steps having the same symbols.

The arithmetic part 210 calculates a tentative spherical power Sr (S401). The calculation is the same as in step S401 described in "4-1. Correction data calculation: spherical power (1)". Then, the arithmetic part 210 specifies a spherical power Ss used in simulation (S451). Usually, Ss is set weaker in correction than Sr (for example, Ss=Sr+5D). The arithmetic part 210 specifies a Landolt's ring (S453) corresponding to visual acuity (for example, Vs=1.0) specified in advance.

In steps S405 to S421, the arithmetic part 210 performs processes such as Landolt's-ring retina image simulation and Landolt's-ring template matching in the same way as in the steps having the same symbols in "4-1. Correction data calculation: spherical power (1)".

In step S421, when the determination part 212 of the arithmetic part 210 determines that simulation has been performed in all directions, the determination part 212 further determines whether detection could be made in the number of directions equal to or more than a half of the specified number of directions (S455). When yes in step S455, the correction-factor setting part 213 sets S=Ss and V=Vs, and specifies a Landolt's ring corresponding to visual acuity Vs=Vs+0.1 (S457). Then, the processing proceeds to step S405, and the image-data generation part 211 performs retina-image simulation according to the specified correction factor and Landolt's ring to obtain target image data, and the processes of step S407 and subsequent steps are executed. When no in step S455, the arithmetic part 210 outputs data (S423). More specifically, the arithmetic part 210 displays, for example, the current spherical power S=Ss, the detected direction of the Landolt's ring, the size V of the Landolt's ring, and simulation results on the display part 230, and stores them in the memory 240.

4-3. Correction Data Calculation (Astigmatism-1)

Figure 12:
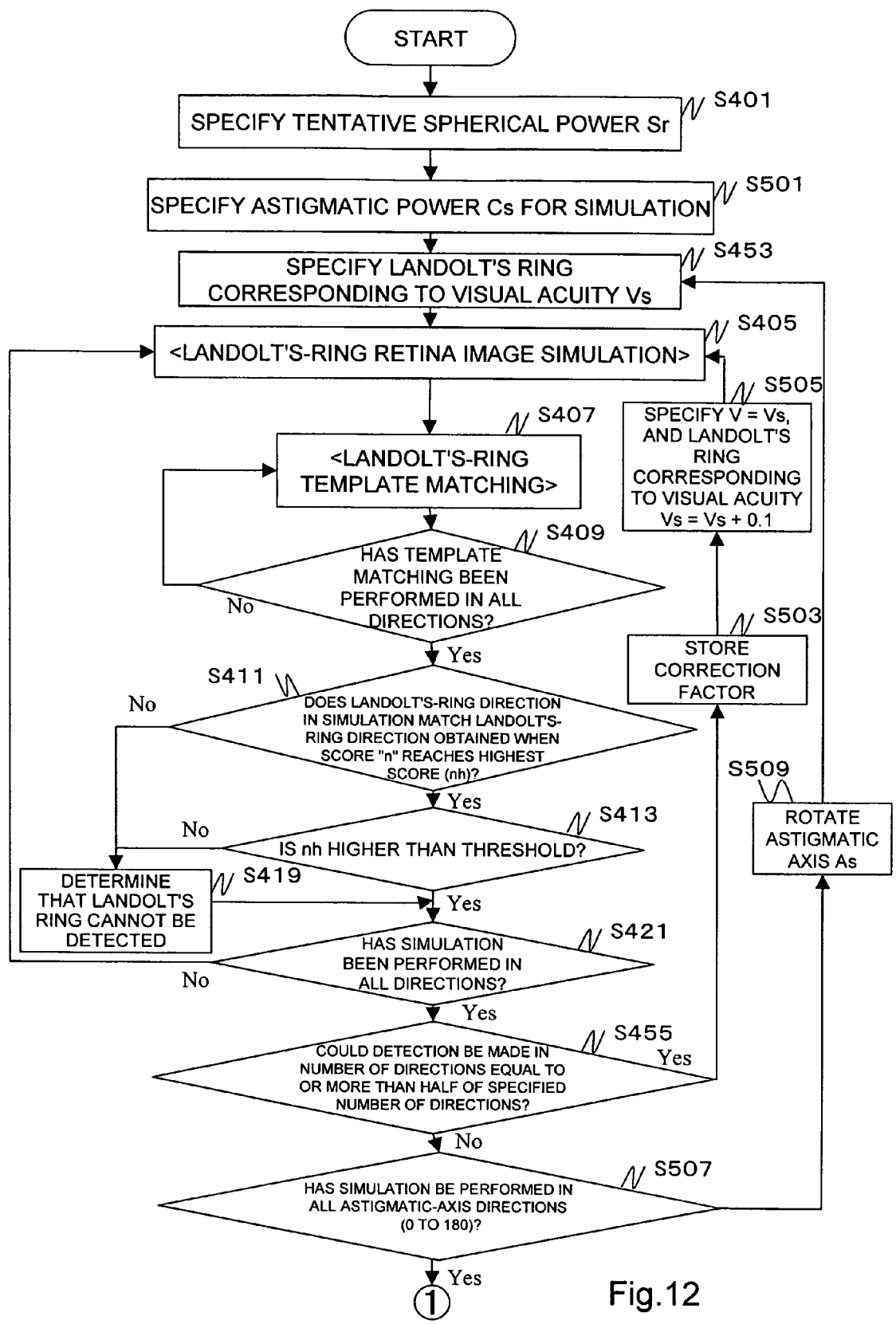
FIG. 12 is a first flowchart of correction-data calculation (astigmatism-1).
Figure 13:
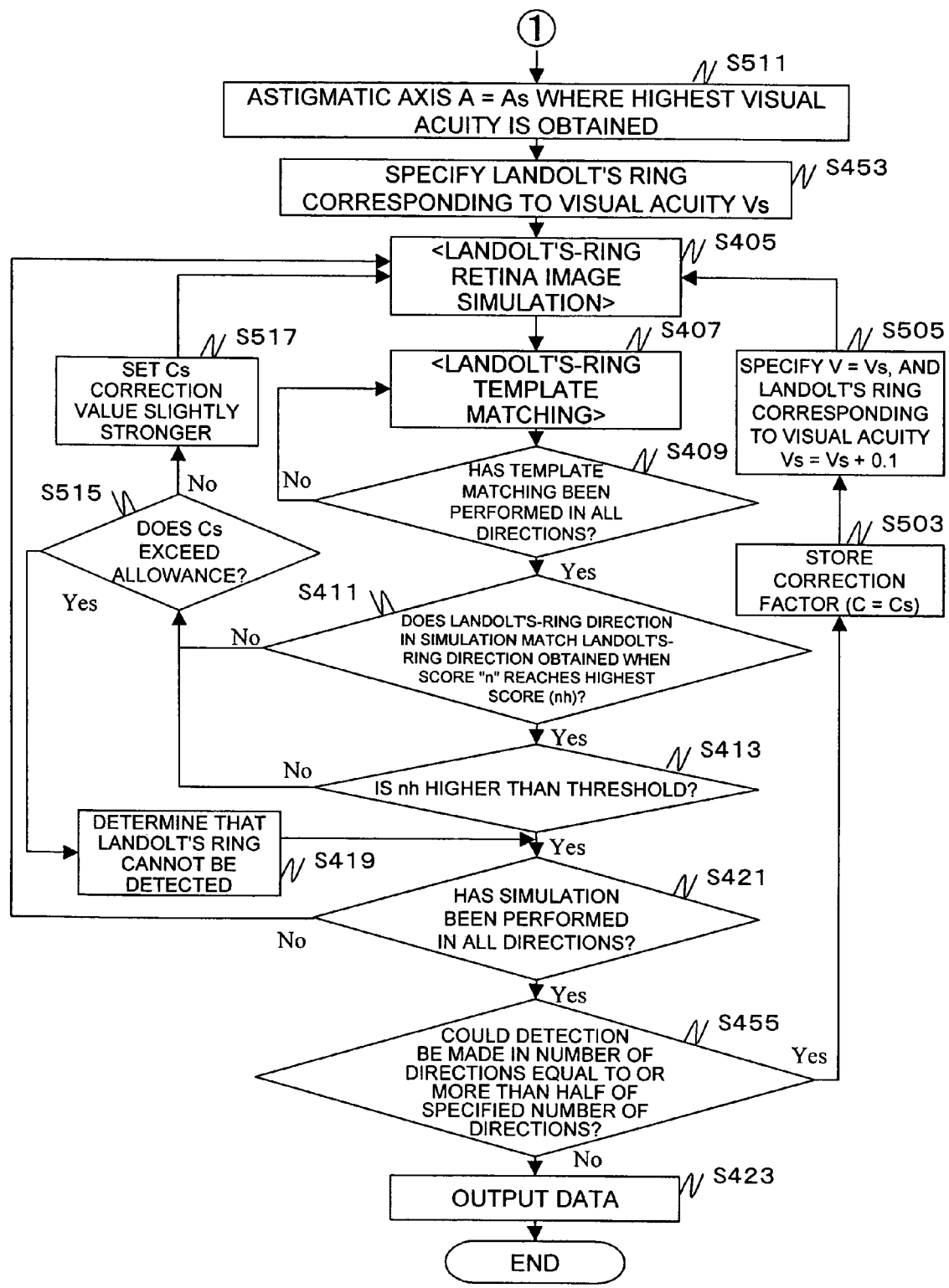
FIG. 13 is a second flowchart of the correction-data calculation (astigmatism-1).

FIG. 12 and FIG. 13 show a flowchart of correction-data calculation (astigmatism-1).

The arithmetic part 210 calculates a tentative spherical power Sr (S401) as in step S401 described above. Then, the arithmetic part 210 specifies an astigmatic power Cs used in simulation (S501). For example, Cs may be set to 0, an astigmatic power C calculated from the refractive power or the wavefront aberrations may be used, or Cs may be obtained by referring to a correspondence table having stored Cs in association with a correction factor such as S or C, or Zernike coefficients, stored in advance in the memory 240. The arithmetic part 210 specifies a Landolt's ring (S453) corresponding to visual acuity (for example, Vs=0.1).

In steps S405 to S413, the arithmetic part 210 performs processes such as Landolt's-ring retina image simulation and Landolt's-ring template matching in the same way as described above.

When no in step S411 or step S413, the determination part 212 determines that the Landolt's ring cannot be detected, and stores the direction and the fact that the Landolt's ring cannot be detected in the direction, in the memory 240.

After step S419, or when yes in step S413, the arithmetic part 210 executes the processes of steps S421 and S455 in the same way as described above.

When it is determined in step S455 that detection could be made in the number of directions equal to or more than a half of the specified number of directions, the arithmetic part 210 stores the specified correction factor in the memory 240 (S503). Then, the correction-factor setting part 213 sets V=Vs, and specifies a Landolt's ring corresponding to visual acuity Vs=Vs+0.1 (S505). Then, the processing proceeds to step S405, and the image-data generation part 211 performs retina-image simulation according to the specified correction factor and Landolt's ring to obtain target image data, and the processes of step S407 and subsequent steps are executed.

When no in step S455, the determination part 212 determines (S507) whether simulation has been performed in all astigmatism-axis angles (0 to 180). If no, the correction-factor setting part 213 rotates the astigmatism-axis angle As (for example, As=As+5) (S509). Then, the processing proceeds to step S453, and the processes of step S453 and subsequent steps are repeatedly executed.

Next, by referring to FIG. 13, when the determination part 212 obtains yes in step S507, the correction-factor setting part 213 of the arithmetic part 210 substitutes As where the highest visual acuity V is obtained, for the astigmatic-axis angle A (S511). When there is a plurality of As's where the highest visual acuity V is obtained, As where the largest number of Landolt's rings can be detected at the visual acuity V is substituted for the astigmatic-axis angle A. When there is also a plurality of such As's, As where the sum of nh's in directions in which Landolt's rings can be detected at the visual acuity V is the largest is specified. With this, the astigmatic-axis angle A is determined.

In steps S453, and S405 to S413, as described in the above-mentioned embodiment, the arithmetic part 210 performs processes such as Landolt's-ring retina image simulation and Landolt's-ring template matching according to the specified Sr, Cs, and A.

If no in step S411 or step S413, the determination part 212 determines (S515) whether Cs exceeds an allowance (for example, Cs−10D) specified in advance. If no, the correction-factor setting part 213 sets the Cs correction factor slightly stronger (for example, Cs=Cs−0.25D) (S517), and the image-data generation part 211 performs Landolt's-ring retina image simulation according to this correction factor (S405). The arithmetic part 210 executes the processes of step S407 and subsequent steps for the target retina image data obtained by the simulation. When yes is step S415, the determination part 212 determines (S419) that the Landolt's ring cannot be detected, and stores the direction and the fact that the Landolt's ring cannot be detected in the direction, in the memory 240.

After step S419, or when yes in step S413, the determination part 212 determines (S421) whether simulation has been performed in all directions of the Landolt's ring. If no, the processing returns to step S405, and the arithmetic part 210 repeats the above-described processes in all directions. When yes in step S421, the arithmetic part 210 determines whether detection could be made in the number of directions equal to or more than a half of the specified number of directions (S455). When yes in step S455, the arithmetic part 210 stores the specified correction factor (C=Cs) in the memory 240 (S503). Then, the correction-factor setting part 213 sets V=Vs, and specifies a Landolt's ring corresponding to visual acuity Vs=Vs+0.1 (S505). Then, the processing proceeds to step S405, and the image-data generation part 211 performs retina-image simulation according to the specified correction factor and Landolt's ring to obtain target image data, and the processes of step S407 and subsequent steps are executed.

When no in step S455, the arithmetic part 210 outputs data (S423). More specifically, the arithmetic part 210 displays the current spherical power S=Ss, the detected direction of the Landolt's ring, the visual acuity V, simulation results, and others on the display part 230, and stores them in the memory 240.

4-4. Correction Data Calculation (Astigmatism-2)

Figure 14:
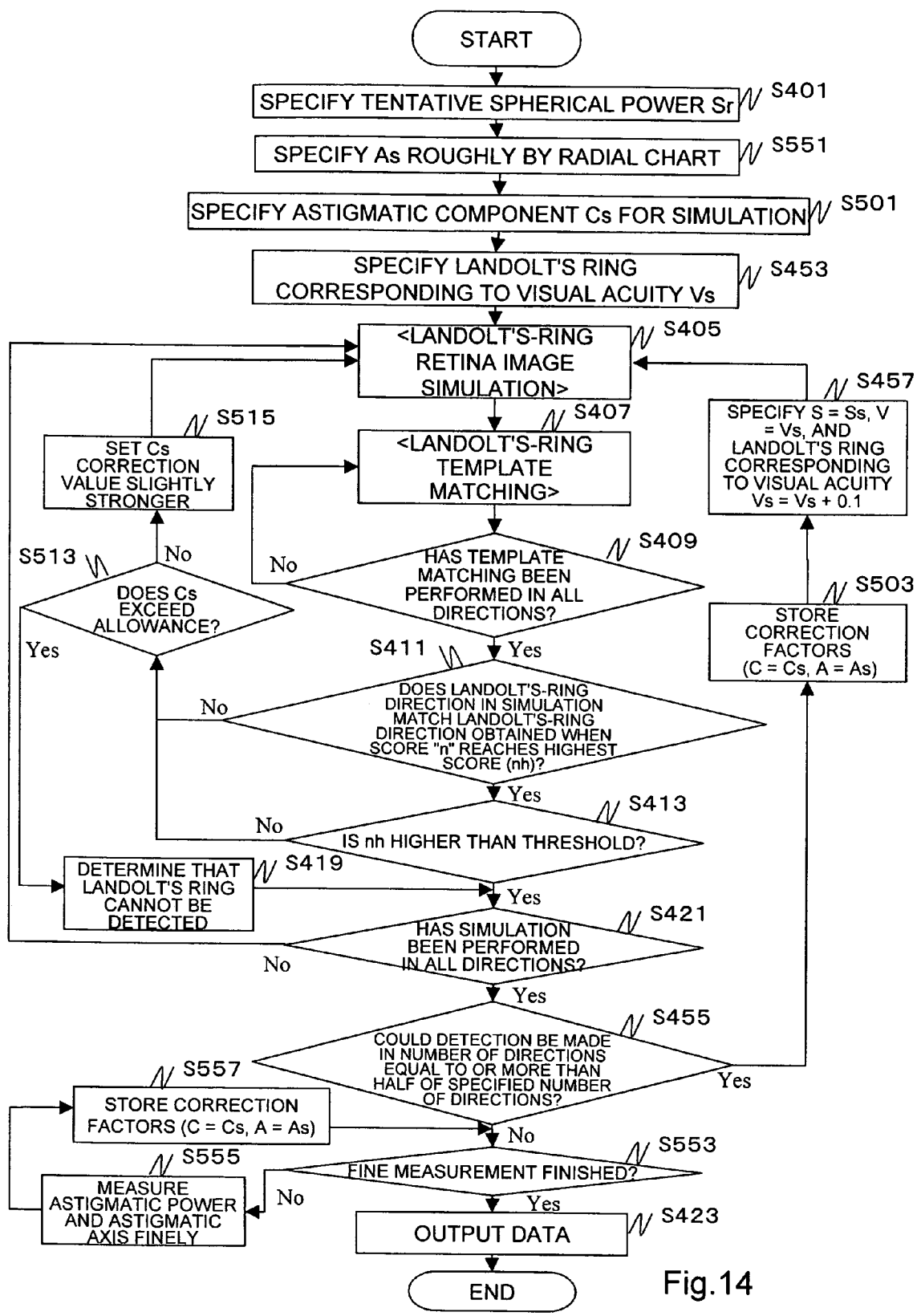
FIG. 14 is a flowchart of correction-data calculation (astigmatism-2).

FIG. 14 shows a flowchart of correction-data calculation (astigmatism-2).

In step S401, the arithmetic part 210 calculates a tentative spherical power Sr as described above. Then, the arithmetic part 210 roughly specifies an axis angle As by using a radial pattern (S551). For example, "As" can be calculated from the wavefront aberrations determined by the Zernike coefficients obtained before. "As" can also be obtained by simulating target retina image data by the use of data indicating the radial pattern instead of the Landolt's ring in the retina-image simulation processing described above. "As" measured in advance by using the radial chart or the like may be input by the input part, or "As" stored in advance in the memory 240 may be read and used. In step S501, as described above, the arithmetic part 210 specifies an astigmatic component Cs for simulation. From step S453 to step S455, as described above, the arithmetic part 210 performs processes such as Landolt's-ring retina image simulation and Landolt's-ring template matching. In step S503, the arithmetic part 210 stores C=Cs and A=As as correction factors.

When it is determined in step S455 that detection could be made in the number of directions equal to or more than a half of the specified number of directions, the arithmetic part 210 determines whether to finish precise measurement (S553). If no, the arithmetic part 210 precisely measures the astigmatic power and the angle of the astigmatic axis (S555). As a precise-measurement method, a known technique can be used, if necessary. For example, measurement apparatuses described in Japanese Examined Patent Application Publication No. Hei-5-9092, Japanese Unexamined Patent Application Publication No. Sho-55-151937, and others can be used to precisely measure the astigmatic power and the angle of the astigmatic axis.

Japanese Examined Patent Application Publication No. Hei-5-9092 describes a refractive-power measuring apparatus capable of precisely measuring the refractive power of an eye under measurement, namely, the spherical power, the cylindrical power, and the angle of the cylindrical axis, by projecting a measurement eyesight target onto the eye under measurement through an optical system with the use of a variable cross-cylinder formed of two cylindrical lenses or toric lenses having refractive powers different in sign and the same in absolute value. The refractive-power measuring apparatus includes a spherical optical system having a variable spherical power, a cylindrical optical system having a variable cylindrical power, and a control section for variably controlling the spherical power and the cylindrical power of both optical systems, and measures the refractive power of the eye under measurement by projecting an measurement eyesight target through both optical systems.

This apparatus includes two toric lenses rotatable about the optical axis of the cylindrical optical system and having refractive powers different in sign, and the control section includes rotation control means and first and second state change means. The rotation control means controls the rotation of the cylindrical optical system such that the intersection angle of the cylindrical axes of the toric lenses is obtained correspondingly to the cylindrical power obtained in rough measurement. The first state change means precisely measures the cylindrical power with the intermediate direction of the intersection angle of the cylindrical axes of the toric lenses being set to a reference line by operating the rotation control means to increase or reduce the intersection angle in a predetermined range with the reference line being set to the center, correspondingly to the cylindrical power obtained by the rough measurement. The second state change means precisely measures the angle of the cylindrical axis by operating the rotation control means to move the toric lenses in the same direction to increase and reduce the angle of the cylindrical axis obtained when the refractive power is roughly measured, in a predetermined range without changing the intersection angle of the cylindrical axes of the toric lenses.

After such appropriate precise measurements, the arithmetic part 210 stores the correction factors (C=Cs and A=As) obtained in the precise measurements, in the memory 240 (S557).

When yes in step S553, the arithmetic part 210 outputs data (S423). More specifically, the arithmetic part 210 displays the current spherical power S, the visual acuity V, the astigmatic components C and A, the detected direction, simulation results, and others on the display part 230, and stores them in the memory 240.

4-5. Correction Data Calculation (Astigmatism-3)

Figure 15:
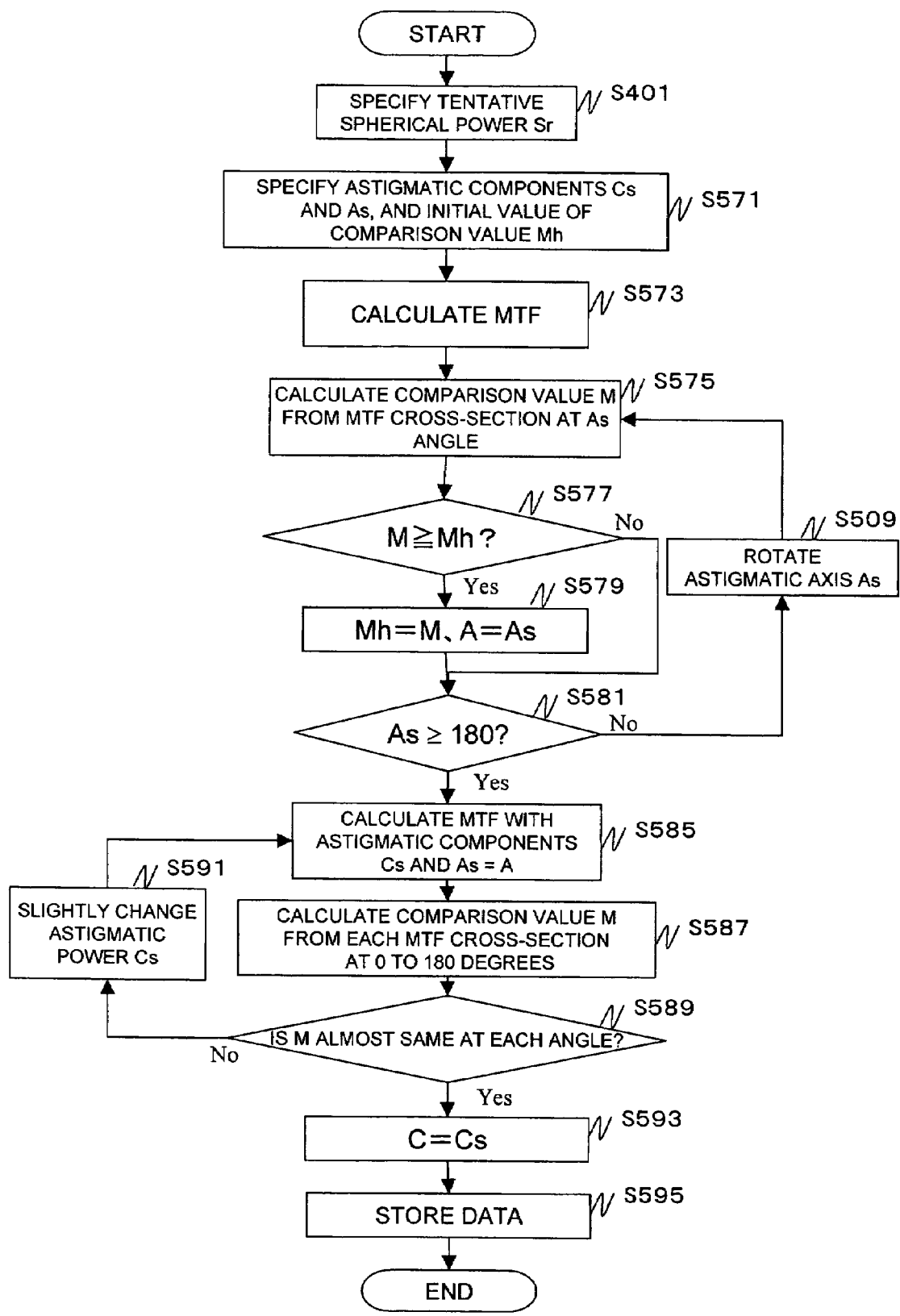
FIG. 15 is a flowchart of correction-data calculation (astigmatism-3).

FIG. 15 shows a flowchart of correction-data calculation (astigmatism-3).

In step S401, as described above, the arithmetic part 210 calculates a tentative spherical power Sr. Then, the arithmetic part 210 initially specifies an astigmatic power Cs and the angle As of an astigmatic axis, both of which are astigmatic components, and a comparison numeral Mh (S571). These values may be stored in advance in the memory 240, or may be input through the input part. The arithmetic part 210 initially specifies, for example, Cs=0, As=0, and Mh=0.

The arithmetic part 210 calculates the MTF (modulation transfer function) (S573) according to the wavefront aberrations obtained before. A specific MTF calculation method will be described later. The arithmetic part 210 calculates a comparison numeral M from an MTF cross-section at the specified angle As of the astigmatic axis (S575). As the comparison numeral M, the total sum of MTF values, an MTF cross-section, or the sum of 3, 6, 12, and 18 cpd, for example, can be used. The arithmetic part 210 stores currently set As and M in the memory 240.

The determination part 212 of the arithmetic part 210 determines whether M≧Mh (S577). If no, the processing proceeds to step S581. If yes, the correction-factor setting part 213 of the arithmetic part 210 sets Mh=M and A=As (S579). Then, the determination part 212 determines whether As is 180 or larger (S581). If no, the correction-factor setting part 213 rotates the angle As of the astigmatic axis (for example, As=As+5) (S509). Then, the arithmetic part 210 goes back to step S575 and repeats the processes to obtain the maximum value of M in an axis-angle range of 0 to 180 degrees and the angle As (weak main longitude line or strong main longitude line) of the astigmatic axis equal to the direction where the maximum value of M is obtained.

If yes in step S581, in other words, if the angle A of the astigmatic axis is obtained, the arithmetic part 210 calculates the MTF according to the astigmatic components Cs and As=A. The arithmetic part 210 further calculates the comparison numeral M from each MTF cross-section at 0 to 180 degrees (for example, at an interval of 5 degrees).

The determination part 212 determines whether the calculated Ms are almost equal at the angles (S589). For example, it can be determined by determining whether the difference between the maximum value of M and the minimum value of M is smaller than a predetermined threshold. If no in step S589, the arithmetic part 210 slightly changes the astigmatic power Cs (for example, Cs=Cs−0.25) (S591), and the processes of step S585 and subsequent steps are repeated. If yes in step S589, the arithmetic part 210 specifies C=Cs (S593).

The arithmetic part 210 stores the astigmatic power C and the angle A of the astigmatic axis obtained, in the memory 240, and displays them on the display part 230, if necessary (S595).

(MTF Calculation)

Next, how the MTF (modulation transfer function) is calculated will be described.

The MTF is an index indicating a spatial-frequency transfer characteristic, and is widely used for expressing the performance of optical systems. How things are seen can be predicted by the MTF, for example, the transfer characteristic of 0 to 100 thick and thin, sine-wave-shaped gratings per one degree obtained. In the present embodiment, a single-color MTF may be used or a white-color MTF may be used, as described below.

First, the single-color MTF is calculated from the wavefront aberrations W(x, y). W(x, y) is an input value (measured value), and corneal wavefront aberrations obtained from the shape of the cornea can also be used for corneal aberration.

The pupil function f(x, y) can be determined from the wavefront aberrations in the following way.

$$f(x, y) = e^{ikW(x, y)}$$

where, i indicates an imaginary number, and k indicates a wave vector ($2\pi/\lambda$).

Fourier transform is applied to the pupil function f(x, y) to obtain a point spread function U(u, v) by amplitude.

$$U(u, v) = \int\int_{-\infty}^{\infty} f(x, y) \exp\left[-\frac{i}{R}\frac{2\pi}{\lambda}(ux+vy)\right] dx dy$$

where, $\lambda$ indicates a wavelength, R indicates the distance between the pupil to the image point (retina), (u, v) indicates the coordinates of the retina on a plane perpendicular to the optical axis and having the image point O on the retina as the origin, and (x, y) indicates the coordinates of the optical system on the pupil plane.

The point spread function U(u, v) by amplitude is multiplied by its complex conjugate to obtain the point spread function (PSF) I(u, v).

$$I(u, v) = U(u, v) U^*(u, v)$$

Fourier transform is applied to the point spread function I(u, v) and (R(r, s)) standardized, which is spatial-frequency transform, to obtain the OTF (optical transfer function).

$$R(r, s) = \int\int_{-\infty}^{\infty} I(u, v) e^{-i2\pi(ru+sv)} du dv$$

where, r and s are variables in the spatial-frequency domain.

$$OTF(u, v) = R(r, s)/|R(0, 0)|$$

Since the magnitude of the OTF is the MTF, the following expression is satisfied.

$$MTF(r, s) = |OTF(u, v)|$$

The white-color MTF is calculated from the single-color MTF, obtained as described above.

To obtain the white-color MTF, the MTF is weighted at each wavelength and added. Since the above-described MTF has a different value at each wavelength, the MTF can be expressed in the following way when the MTF at a wavelength $\lambda$ is indicated by $MTF_\lambda$.

$$MTF(r, s) = \frac{\int \omega_\lambda MTF_\lambda(r, s) d\lambda}{\int \omega_\lambda d\lambda}$$

The MTF is highly weighted at visible-light wavelengths, and the calculation is made.

More specifically, the MTF is obtained in the following way when it is assumed, for example, that the three primary colors (R, G, and B) are specified such that red light has a wavelength of 656.27 nm with a weight of 1, green light has a wavelength of 587.56 nm with a weight of 2, and blue light has a wavelength of 486.13 nm with a weight of 1.

$$MTF(r, s) = (1 \times MTF_{656.27} + 2 \times MTF_{587.56} + 1 \times MTF_{486.13})/(1+2+1)$$

Since the white-light MTF is measured only at one wavelength (840 nm), calibration may be performed for other wavelengths according to the result of measurement, as compensation, to obtain the MTF at each wavelength. More specifically, when the eye optical characteristic measuring apparatus measures eye aberration, for example, at 840 nm, color aberration $W_A(x, y)$ corresponding to a shift from the wavefront aberrations $W_{840}(x, y)$ at a wavelength of 840 nm is measured with the use of an eye model, $W_{840}(x, y)$ is added to the color aberration $W_A(x, y)$, and the MTF is calculated at each wavelength from this wavefront aberrations in the following way.

$$W_\lambda(x, y) = W_{840}(x, y) + W_A(x, y)$$

5. Correction-Factor Determination Method (Second Embodiment)

Figure 16:
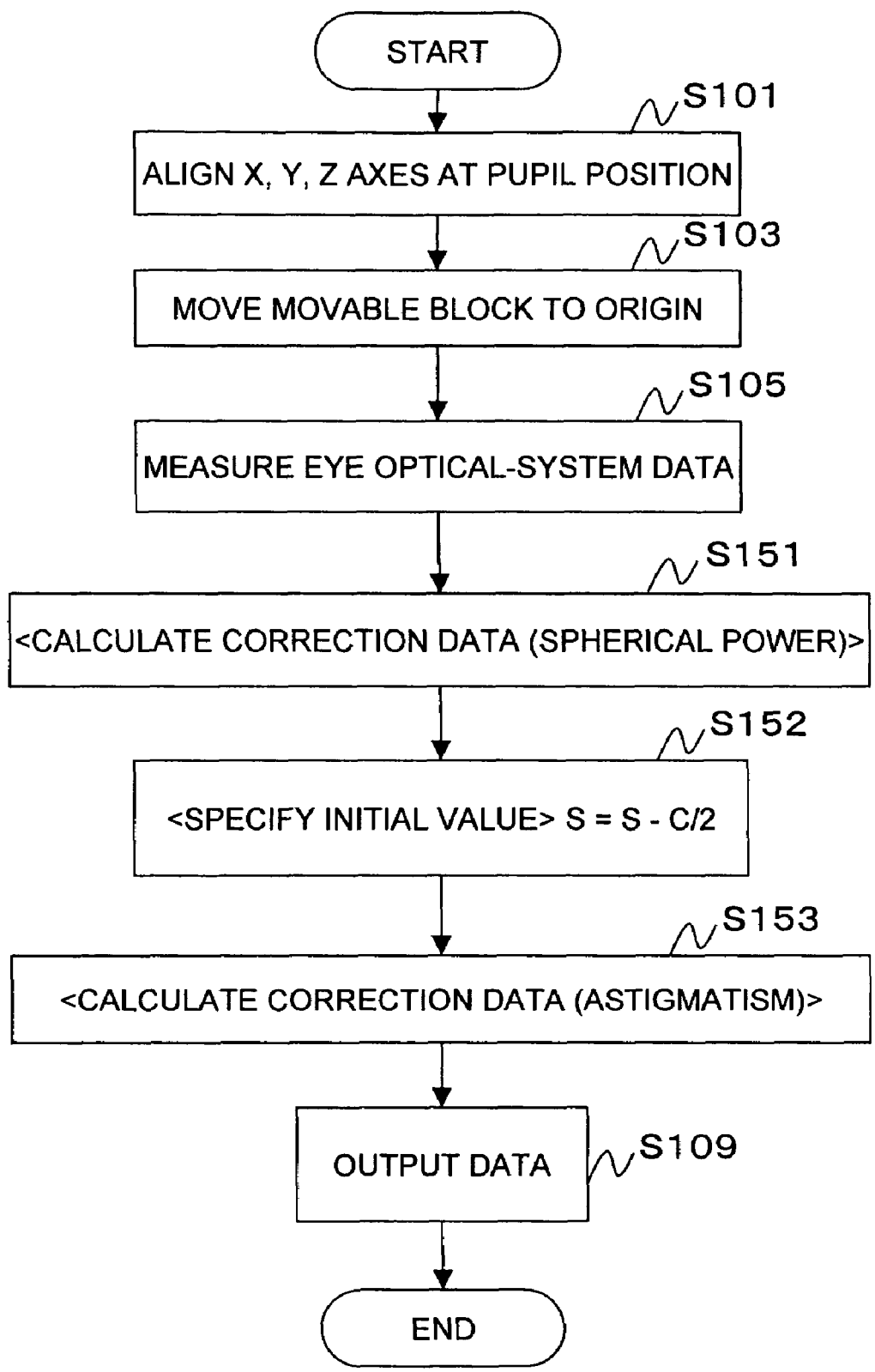
FIG. 16 is a flowchart of a correction-factor determination method according to a second embodiment.

FIG. 16 is a flowchart of a correction-factor determination method according to a second embodiment. Processes at steps S101 to S105 are the same as in the first embodiment. Then, the arithmetic part 210 calculates correction data for the spherical power (S151). As a specific process thereof, a process described in "4-1. Correction data calculation (spherical power-1)" or "4-2. Correction data calculation (spherical power-2)" can be used.

Next, the correction-factor setting part 213 of the arithmetic part 210 subtracts a value (in this case, C/2) corresponding to the astigmatic power C from the obtained spherical power S to specify the initial value of the spherical power S. This is performed because the fact that the astigmatic power is obtained at a position where the back focal line is almost on the retina is taken into account. The value of C may be obtained from the refractive power or the wavefront aberrations obtained in step S105, or appropriately specified in advance. Then, the arithmetic part 210 calculates correction data for the astigmatic components (S153). As a specific process thereof, a process described in "4-3. Correction data calculation (astigmatism-1)", "4-4. Correction data calculation (astigmatism-2)", or "4-5. Correction data calculation (astigmatism-3)" can be used.

Then, in step S109, the arithmetic part 210 outputs data in the same way as in the first embodiment.

6. Correction-Factor Determination Method (Third Embodiment)

Figure 17:
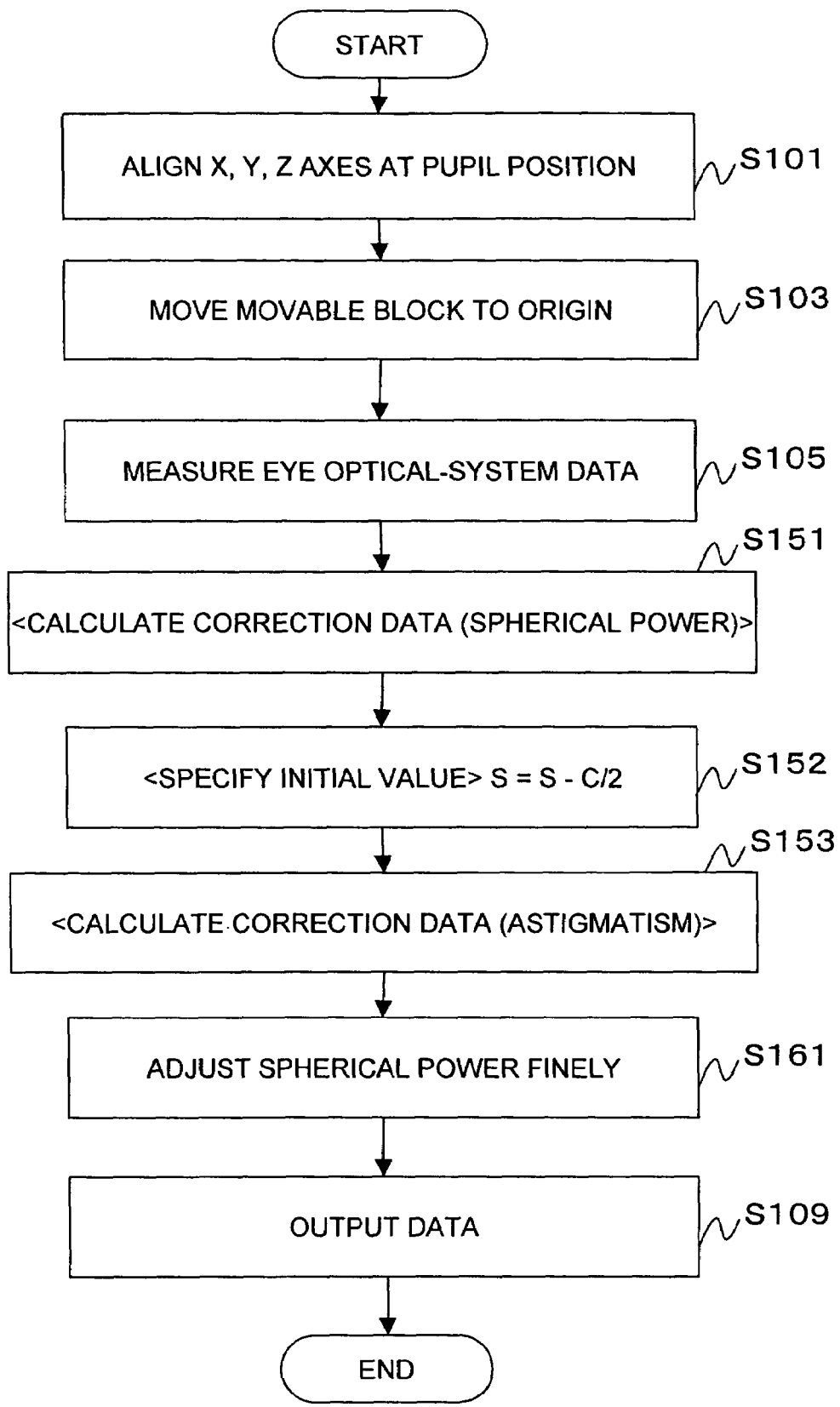
FIG. 17 is a flowchart of a correction-factor determination method according to a third embodiment.

FIG. 17 is a flowchart of a correction-factor determination method according to a third embodiment. Processes at steps S101 to S153 are the same as in the second embodiment. Then, the arithmetic part 210 finely adjusts the spherical power (S161), and in step S109, the arithmetic part 210 outputs data in the same way as in the above-described embodiment.

(Spherical-Power Fine Adjustment)

Figure 18:
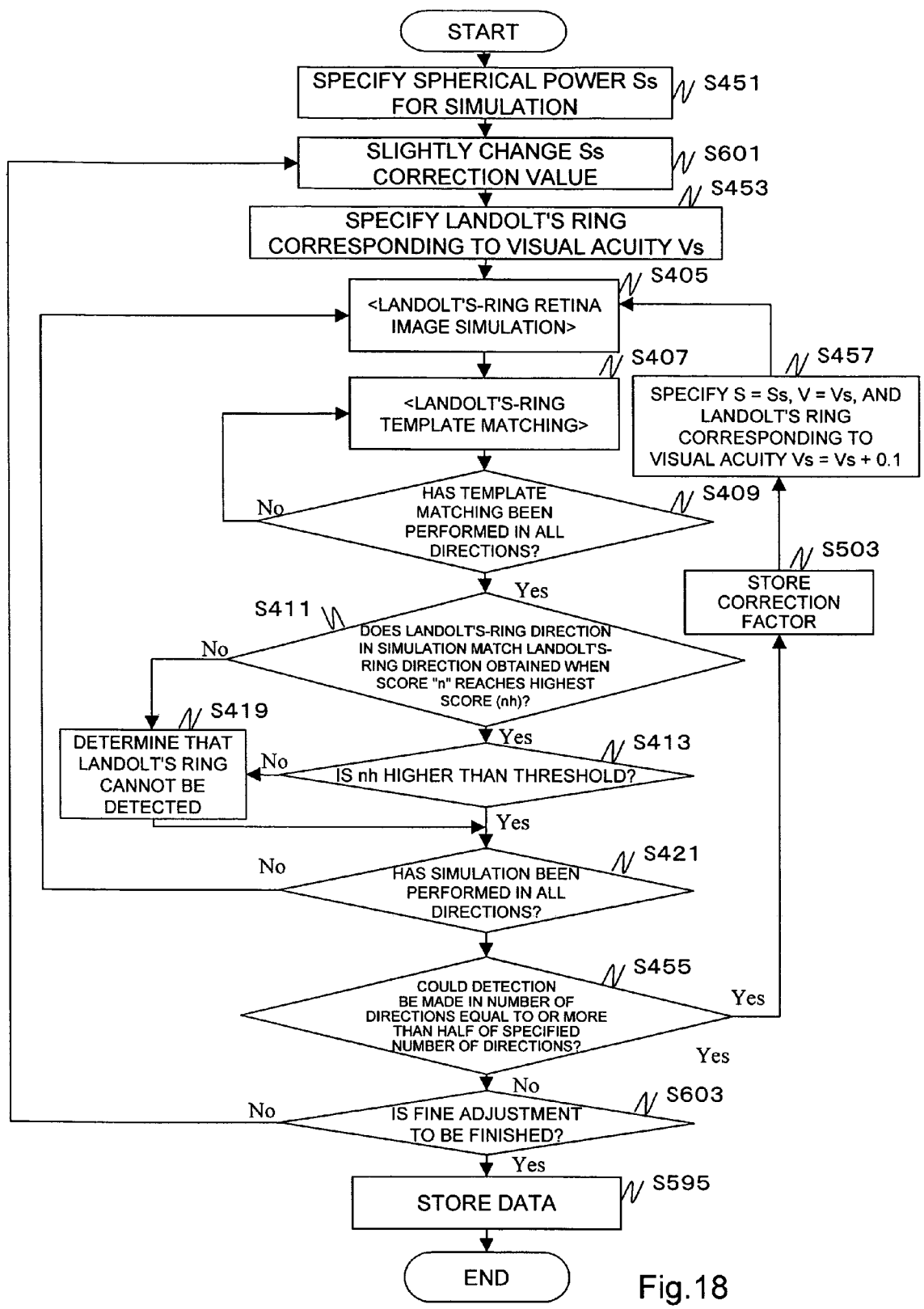
FIG. 18 is a flowchart of spherical-power fine adjustment.
Figure 19:
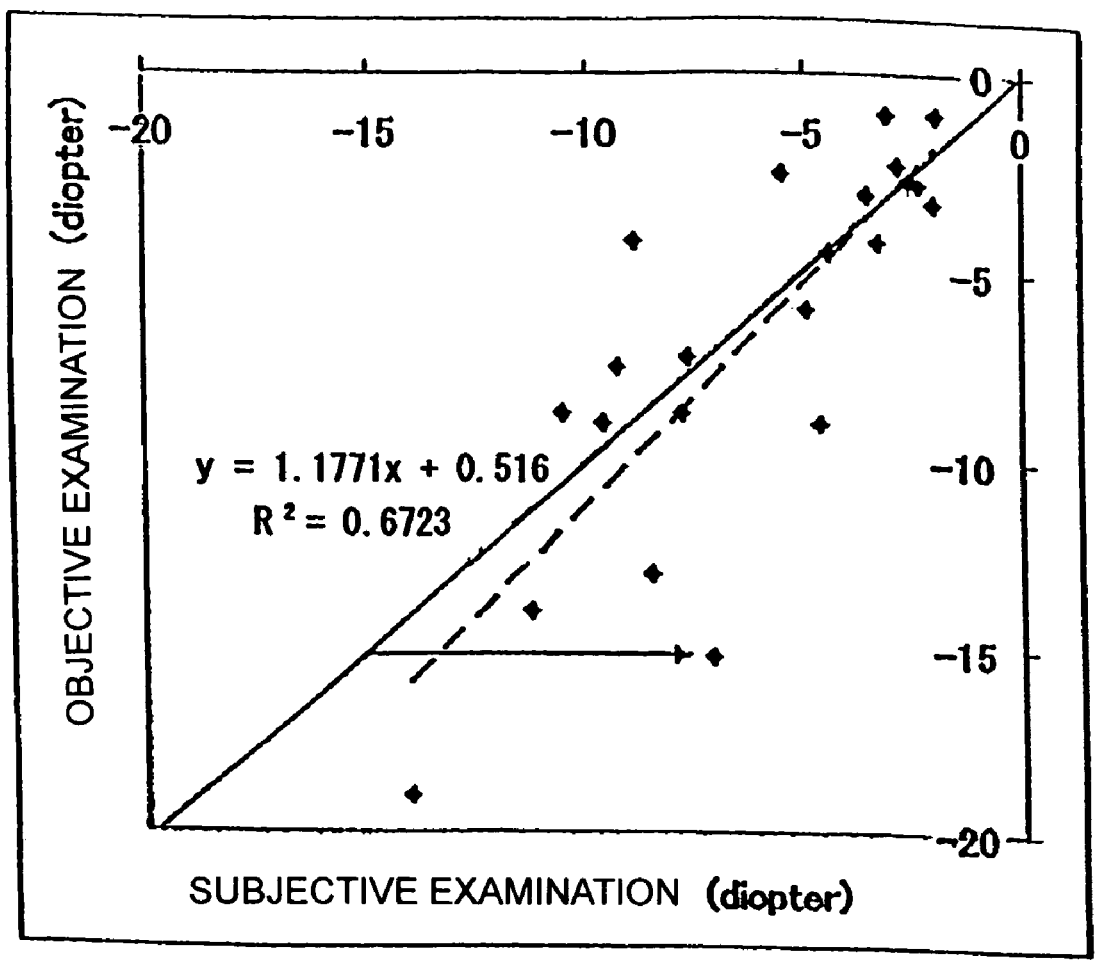
FIG. 19 is a comparison view of an objective examination and a subjective examination.

FIG. 18 shows a flowchart of spherical-power fine adjustment.

In step S451, as described above, the arithmetic part 210 specifies a spherical power Ss used in simulation according to the calculated S, C, and A. Then, the arithmetic part 210 slightly changes the correction value of Ss (for example, Ss−0.25D, Ss+0.25D) (S601). In this case, slightly changed Ss should fall in Ss±nΔS, a range of change specified in advance. For example, when ΔS=0.2 and "n"=0, 1, 2, and 3, changed values would be Ss−0.6, Ss−0.4, Ss−0.2, Ss, Ss+0.2, Ss+0.4, and Ss+0.6.

In steps S405 to S413, the arithmetic part 210 performs processes such as Landolt's-ring retina image simulation and Landolt's-ring template matching (S407) as described in the above-mentioned embodiments. When the determination part 212 determines no in step S411 or step S413, the arithmetic part 210 determines that the Landolt's ring cannot be detected (S419). The arithmetic part 210 stores the direction and the fact that the Landolt's ring cannot be detected in the direction, in the memory 240.

Steps S421, S455, and S457 are the same as those described above.

When the determination part 212 determines in step S455 that detection could be made in the number of directions equal to or more than a half of the specified number of directions, it is determined whether to finish fine adjustment (S603). If no, the processing proceeds to step S601, the correction value of the spherical power Ss is slightly changed, and the processes of step S453 and subsequent steps are repeated. In the process of step S503, the highest visual acuity Vs, the number of directions where detection could be made, nh at the directions where detection could be made are stored in the memory 240 for each Ss, which has been slightly changed.

If yes in step S603, the arithmetic part 210 stores data in the memory 240 (S595). The arithmetic part 210 stores the results (for example, if the visual acuity is improved when S is increased, then the increased S or if the visual acuity is not changed when S is reduced, then the reduced S), obtained by the fine adjustment performed in step S601. The arithmetic part 210 can, for example, pick up spherical powers corresponding to a specified visual acuity or higher from the memory 240, and store in the memory 240 the weakest spherical power corresponding to a specified visual acuity as a value obtained by finely adjusting picked-up data.

7. Additional Note

A correction-data measuring method or a correction-data measuring apparatus and system according to the present invention can be provided by a correction-data measuring program for making a computer execute the procedure of the method or the apparatus and system, a computer-readable recording medium having stored thereon the correction-data measuring program, a program product which includes the correction-data measuring program and can be loaded to an internal memory of a computer, a computer such as a server which includes the program, and others.

Measurement data which indicates the wavefront aberrations of the eye under measurement is obtained by the optical system 100 shown in FIG. 1. The apparatus therefor is not limited to this. An Aberrometer and others can be used.

INDUSTRIAL APPLICABILITY

According to the present invention, a human observer model, for example, is evaluated from a measurement result obtained by an eye-characteristics measuring apparatus capable of measuring even higher-order aberrations, not only when higher-order aberrations, which correspond to a complete objective correction, are used but also when lower-order aberrations are added, a lower-order aberration amount which, for example, improves how an image is seen is calculated, and the data of correction factors such as S, C, and A is obtained at that time to allow a result close to a subjective value to be obtained.

The invention claimed is:

1. A correction-factor determination apparatus comprising:
   an image-data generation section for performing simulation of how an eyesight-test-chart target is seen, according to measurement data which indicates at least the wavefront aberrations of an eye under measurement, with a correction factor for correcting refraction being taken into account, to generate target retina image data;
   a correction-factor setting section for specifying a correction factor to be given to the image-data generation section; and
   a determination section for determining whether the specified correction factor is appropriate, according to corrected target retina image data generated by the image-data generation section and corrected by the correction factor specified by the correction-factor setting section,
   wherein the correction-factor setting section specifies the correction factor according to a result obtained by the determination section, and the correction-factor setting section changes the correction factor by the correction-factor setting section until the determination section determines that the correction factor is appropriate.

2. A correction-factor determination apparatus according to claim 1, wherein the correction factor includes one of or a combination of plurality of a spherical power, an astigmatic power and the angle of an astigmatic axis.

3. A correction-factor determination apparatus according to claim 2, wherein
   the correction-factor setting section changes the correction factor in the order of the spherical power, the angle of the astigmatic axis, and the astigmatic power, and
   the determination section determines whether the specified correction factor is appropriate in the order of the spherical power, the angle of the astigmatic axis, and the astigmatic power.

4. A correction-factor determination apparatus according to claim 2, wherein, when the spherical power and/or the astigmatic power is selected as the correction factor, the image-data generation section sequentially changes the eyesight-test-chart target with which the simulation is performed to eyesight-test-chart targets having different sizes, and performs the simulation of how the eyesight-test-chart target is seen to generate the target retina image data.

5. A correction-factor determination apparatus according to claim 2, wherein the eyesight-test-chart target with which the simulation is performed by the image-data generation section is a Landolt's ring target when it is determined whether the spherical power or the astigmatic power is appropriate.

6. A correction-factor determination apparatus according to claim 1, wherein the determination section determines whether the specified correction factor is appropriate, by comparing a correlation degree of predetermined eyesight-test-chart-target matching pattern data with the target retina image data obtained by the simulation.

7. A correction-factor determination apparatus according to claim 6, wherein the determination section performs determination with template matching by applying two-dimensional Fourier transform to the spatial frequency of a template and multiplying the resultant by the spatial frequency distribution of a retina image.

8. A correction-factor determination apparatus according to claim 6, wherein the image-data generation section calculates a pupil function from the wavefront aberrations, calculates the luminance distribution function of an eyesight target, multiplies the luminance distribution function by the spatial frequency distribution of an eye, and applies two-dimensional inverse Fourier transform to the resultant to obtain target retina image data simulated measurement data which indicates the refractive power distribution of the eye under measurement and/or target retina image data corrected by the specified correction factor.

9. A correction-factor determination apparatus according to claim 1, wherein the image-data generation section generates MTF data as the simulation of how the eyesight-test-chart target is seen, with the measurement data which indicates at least the wavefront aberrations of the eye under measurement, and the correction factor for correcting refraction being taken into account, and the determination section determines from the generated MTF data whether the correction factor is appropriate.

10. A correction-factor determination apparatus according to claim 1, wherein the correction-factor setting section performs correction from a weak correction point.

11. A correction-factor determination apparatus according to claim 1, wherein the correction-factor setting section performs correction according to a subjective measurement procedure.

12. A correction-factor determination apparatus according to claim 1, further comprising a display section for displaying the result of determination made by the determination section and the target retina image data generated by the image-data generation section, or for displaying target retina image data obtained with an appropriate correction factor and a correction factor close thereto.

13. A correction-factor determination method including:

a step of generating target retina image data by performing simulation of how an eyesight-test-chart target is seen, according to measurement data which indicates at least the wavefront aberrations of an eye under measurement, with a correction factor for correcting refraction being taken into account;

a step of specifying a correction factor for generating the target retina image data; and a step of determining whether the specified correction factor is appropriate, according to corrected target retina image data generated in the step of generating the target retina image data and corrected by the correction factor specified in the step of specifying the correction factor, wherein the correction factor is specified in the step of specifying the correction factor, according to a result obtained in the step of determining, and the correction factor is changed in the step of specifying the correction factor until it is determined that the correction factor is appropriate in the step of determining.

14. A correction-factor determination method according to claim 13, wherein the correction factor includes one of or a combination of plurality of a spherical power, an astigmatic power, and the angle of an astigmatic axis.

15. A correction-factor determination method according to claim 14, wherein, when the spherical power and/or the astigmatic power is selected as the correction factor, the eyesight-test-chart target with which the simulation is performed is sequentially changed to eyesight-test-chart targets having different sizes, and performs the simulation of how the eyesight-test-chart target is seen to generate the target retina image data, in the step of generating the target retina image data.

16. A correction-factor determination method according to claim 14, wherein the eyesight-test-chart target with which the simulation is performed in the step of generating the target retina image data is a Landolt's ring target when it is determined whether the spherical power or the astigmatic power is appropriate.

17. A correction-factor determination method according to claim 14, wherein the correction factor is changed in the order of the spherical power, the angle of the astigmatic axis, and the astigmatic power in the step of specifying the correction factor, and it is determined whether the correction factor is appropriate in the order of the spherical power, the angle of the astigmatic axis, and the astigmatic power in the step of determining.

18. A correction-factor determination method according to claim 13, wherein it is determined whether the specified correction factor is appropriate, by comparing a correlation degree of predetermined eyesight-test-chart-target matching pattern data with the target retina image data simulated, in the step of determining.

19. A correction-factor determination method according to claim 18, wherein determination is performed with template matching by applying two-dimensional Fourier transform to the spatial frequency of a template and multiplying the resultant by the spatial frequency distribution of a retina image, in the step of determining.

20. A correction-factor determination method according to claim 18, wherein a pupil function is calculated from the wavefront aberrations, the luminance distribution function of an eyesight target is calculated, the luminance distribution function is multiplied the resultant by the spatial frequency distribution of an eye, and two-dimensional inverse Fourier transform is applied to the resultant to obtain target retina image data obtained by simulating measurement data which indicates the refractive power distribution of the eye under measurement and/or target retina image data corrected by the specified correction factor, in the step of generating the target retina image data.

21. A correction-factor determination method according to claim 13, wherein

MTF data is generated as the simulation of how the eyesight-test-chart target is seen, with the measurement data which indicates at least the wavefront aberrations of the eye under measurement, and the correction factor for correcting refraction being taken into account, in the step of generating the target retina image data, and it is determined from the generated MTF data whether the correction factor is appropriate, in the step of determining.

22. A correction-factor determination method according to claim 13, wherein correction is performed from a weak correction point in the step of specifying the correction factor.

23. A correction-factor determination method according to claim 13, wherein correction is performed according to a subjective measurement procedure in the step of specifying the correction factor.

24. A correction-factor determination method according to claim 13, further including a step of precisely measuring an astigmatic power and the angle of an astigmatic axis.

25. A correction-factor determination method according to claim 13, further including a spherical-power fine-adjustment step of finely adjusting an obtained spherical power to obtain a spherical power which causes to obtain a further high visual acuity value.

26. A correction-factor determination method including:
a step of calculating which uses a first spherical power included in measurement data which indicates the refractive-power distribution of an eye under measurement, as a correction factor to calculate a second spherical power by the correction-factor determination method described in claim 13;

a step of obtaining the third spherical power from the second spherical power by compensating a value based on a first astigmatic power included in the measurement data which indicates the refractive-power distribution of the eye under measurement; and a step of calculating which uses the third spherical power as a correction factor to calculate a second astigmatic power by the correction-factor determination method described in claim 13.

27. A correction-factor determination method according to claim 13, wherein the wavefront aberrations comprise higher-order aberration.

* * * * *